(12) United States Patent
Houser et al.

(10) Patent No.: US 10,881,448 B2
(45) Date of Patent: Jan. 5, 2021

(54) CAM DRIVEN COUPLING BETWEEN ULTRASONIC TRANSDUCER AND WAVEGUIDE IN SURGICAL INSTRUMENT

(71) Applicant: Ethicon Endo-Surgery, Inc, Cincinnati, OH (US)

(72) Inventors: Kevin L Houser, Springboro, OH (US); William D. Dannaher, Cincinnati, OH (US); Stephen J. Balek, Springboro, OH (US); Wells D. Haberstich, Loveland, OH (US); Matthew C. Miller, Cincinnati, OH (US); Scott A. Woodruff, Boston, MA (US)

(73) Assignee: Ethicon LLC, Guaynabo, PR (US)

( * ) Notice: Subject to any disclaimer, the term of this patent is extended or adjusted under 35 U.S.C. 154(b) by 1362 days.

(21) Appl. No.: 14/788,915

(22) Filed: Jul. 1, 2015

(65) Prior Publication Data
US 2015/0305763 A1  Oct. 29, 2015

Related U.S. Application Data

(62) Division of application No. 13/274,496, filed on Oct. 17, 2011, now abandoned.
(Continued)

(51) Int. Cl.
*A61B 17/00* (2006.01)
*A61B 18/14* (2006.01)
(Continued)

(52) U.S. Cl.
CPC .... *A61B 18/1442* (2013.01); *A61B 17/00234* (2013.01); *A61B 17/2812* (2013.01);
(Continued)

(58) Field of Classification Search
CPC ..................... A61B 1/00112; A61B 1/00121
See application file for complete search history.

(56) References Cited

U.S. PATENT DOCUMENTS

| 1,754,806 A | 4/1930 | Stevenson |
| 2,340,822 A | 2/1944 | Scott |

(Continued)

FOREIGN PATENT DOCUMENTS

| DE | 102008051866 | 10/2010 |
| DE | 102009013034 | 10/2010 |

(Continued)

OTHER PUBLICATIONS

Dietz, T. et al., Partially Implantable Vibrating Ossicular Prosthesis, Transducers'97, vol. 1, International Conference on Solid State Sensors and Actuators, (Jun. 16-19, 1997) pp. 433-436 (Abstract).
(Continued)

*Primary Examiner* — Rajeev P Siripurapu
(74) *Attorney, Agent, or Firm* — Frost Brown Todd LLC

(57) ABSTRACT

A surgical instrument includes a body assembly, a waveguide, a transducer, and a coupling assembly. In some versions the coupling assembly translates the transducer to couple the transducer to the waveguide. For instance, a gear having arcuate troughs may engage pins on the transducer and/or waveguide to mate the transducer to waveguide. A pawl may selectively engage and prevent rotation of the gear. Alternatively, lever arms may cam the transducer into the waveguide. The lever arms may selectively couple to a casing to prevent decoupling of the transducer and waveguide. In another configuration, a locking tab can be slid and locked into a slot to couple the transducer and waveguide. Further still, levers with self-locking pins may engage and couple the transducer to the waveguide. In another version,
(Continued)

a rotatable body portion may engage a tab on the transducer to rotate and couple the transducer to the waveguide.

20 Claims, 17 Drawing Sheets

Related U.S. Application Data

(60) Provisional application No. 61/487,846, filed on May 19, 2011, provisional application No. 61/410,603, filed on Nov. 5, 2010.

(51) Int. Cl.

| | |
|---|---|
| *A61B 90/40* | (2016.01) |
| *A61B 18/00* | (2006.01) |
| *A61B 18/04* | (2006.01) |
| *A61B 18/12* | (2006.01) |
| *H02J 7/00* | (2006.01) |
| *H01M 2/10* | (2006.01) |
| *G16H 40/63* | (2018.01) |
| *A61B 17/32* | (2006.01) |
| *H01M 10/42* | (2006.01) |
| *A61B 50/30* | (2016.01) |
| *G16H 20/40* | (2018.01) |
| *A61B 34/00* | (2016.01) |
| *A61B 46/10* | (2016.01) |
| *A61B 90/00* | (2016.01) |
| *A61B 17/28* | (2006.01) |
| *A61N 7/00* | (2006.01) |
| *H01M 2/26* | (2006.01) |
| *H01M 10/46* | (2006.01) |
| *H01M 10/48* | (2006.01) |
| *H02J 7/02* | (2016.01) |
| *A61B 17/064* | (2006.01) |
| *A61B 17/285* | (2006.01) |
| *A61B 17/29* | (2006.01) |
| *A61B 50/00* | (2016.01) |

(52) U.S. Cl.
CPC ............... *A61B 17/320068* (2013.01); *A61B 17/320092* (2013.01); *A61B 18/00* (2013.01); *A61B 18/04* (2013.01); *A61B 18/12* (2013.01); *A61B 18/1206* (2013.01); *A61B 18/14* (2013.01); *A61B 18/1445* (2013.01); *A61B 34/25* (2016.02); *A61B 46/10* (2016.02); *A61B 50/30* (2016.02); *A61B 90/08* (2016.02); *A61B 90/40* (2016.02); *A61N 7/00* (2013.01); *G16H 20/40* (2018.01); *G16H 40/63* (2018.01); *H01M 2/10* (2013.01); *H01M 2/1016* (2013.01); *H01M 2/1022* (2013.01); *H01M 2/26* (2013.01); *H01M 10/425* (2013.01); *H01M 10/46* (2013.01); *H01M 10/48* (2013.01); *H02J 7/0044* (2013.01); *H02J 7/0045* (2013.01); *H02J 7/0047* (2013.01); *H02J 7/025* (2013.01); *A61B 17/064* (2013.01); *A61B 17/285* (2013.01); *A61B 18/1233* (2013.01); *A61B 2017/00017* (2013.01); *A61B 2017/0046* (2013.01); *A61B 2017/0084* (2013.01); *A61B 2017/00084* (2013.01); *A61B 2017/00398* (2013.01); *A61B 2017/00473* (2013.01); *A61B 2017/00477* (2013.01); *A61B 2017/00482* (2013.01); *A61B 2017/00734* (2013.01); *A61B 2017/291* (2013.01); *A61B 2017/293* (2013.01); *A61B 2017/294* (2013.01); *A61B 2017/2929* (2013.01); *A61B 2017/2931* (2013.01); *A61B 2017/2933* (2013.01); *A61B 2017/320069* (2017.08); *A61B 2017/320071* (2017.08); *A61B 2017/320094* (2017.08); *A61B 2017/320095* (2017.08); *A61B 2018/0019* (2013.01); *A61B 2018/00178* (2013.01); *A61B 2018/00589* (2013.01); *A61B 2018/00595* (2013.01); *A61B 2018/00601* (2013.01); *A61B 2018/00607* (2013.01); *A61B 2018/00702* (2013.01); *A61B 2018/00791* (2013.01); *A61B 2018/00988* (2013.01); *A61B 2018/126* (2013.01); *A61B 2018/1226* (2013.01); *A61B 2018/1253* (2013.01); *A61B 2018/1412* (2013.01); *A61B 2018/1455* (2013.01); *A61B 2050/005* (2016.02); *A61B 2050/008* (2016.02); *A61B 2050/0065* (2016.02); *A61B 2050/0067* (2016.02); *A61B 2050/0076* (2016.02); *A61B 2050/3007* (2016.02); *A61B 2050/3008* (2016.02); *A61B 2090/0803* (2016.02); *A61B 2090/0813* (2016.02); *A61B 2090/0814* (2016.02); *H01M 2220/30* (2013.01); *H02J 7/0048* (2020.01); *Y10T 29/49005* (2015.01); *Y10T 29/49895* (2015.01); *Y10T 29/53913* (2015.01)

(56) References Cited

U.S. PATENT DOCUMENTS

| | | |
|---|---|---|
| 3,297,192 A | 1/1967 | Swett |
| 3,419,198 A | 12/1968 | Pettersen |
| 3,619,671 A | 11/1971 | Shoh |
| 3,806,225 A * | 4/1974 | Codrino ............... G02B 6/3869 385/88 |
| 4,034,762 A | 7/1977 | Cosens et al. |
| 4,057,220 A | 11/1977 | Kudlacek |
| 4,535,773 A | 8/1985 | Yoon |
| 4,641,076 A | 2/1987 | Linden |
| 4,662,068 A | 5/1987 | Polonsky |
| 4,666,037 A | 5/1987 | Weissman |
| 4,685,459 A | 8/1987 | Koch et al. |
| 4,717,018 A | 1/1988 | Sacherer et al. |
| 4,717,050 A | 1/1988 | Wright |
| 4,721,097 A | 1/1988 | D'Amelio |
| 4,768,969 A | 9/1988 | Bauer et al. |
| 4,800,878 A | 1/1989 | Cartmell |
| 4,844,259 A | 7/1989 | Glowczewskie, Jr. et al. |
| 4,878,493 A | 11/1989 | Pasternak et al. |
| 5,071,417 A | 12/1991 | Sinofsky |
| 5,107,155 A | 4/1992 | Yamaguchi |
| 5,144,771 A | 9/1992 | Miwa |
| 5,169,733 A | 12/1992 | Savovic et al. |
| 5,176,677 A | 1/1993 | Wuchinich |
| 5,246,109 A | 9/1993 | Markle et al. |
| 5,273,177 A | 12/1993 | Campbell |
| 5,277,694 A | 1/1994 | Leysieffer et al. |
| 5,308,358 A | 5/1994 | Bond et al. |
| 5,317,485 A * | 5/1994 | Merjanian ............ G02B 6/3813 362/457 |
| 5,322,055 A | 6/1994 | Davison et al. |
| 5,339,799 A | 8/1994 | Kami et al. |
| 5,358,508 A | 10/1994 | Cobb et al. |
| 5,361,902 A | 11/1994 | Abidin et al. |
| 5,429,229 A | 7/1995 | Chester et al. |
| 5,449,370 A | 9/1995 | Vaitekunas |
| 5,454,378 A | 10/1995 | Palmer et al. |
| 5,501,607 A | 3/1996 | Yoshioka et al. |
| 5,507,297 A | 4/1996 | Slater et al. |
| 5,561,881 A | 10/1996 | Klinger et al. |
| 5,578,052 A | 11/1996 | Koros et al. |
| 5,580,258 A | 12/1996 | Wakata |
| 5,582,617 A | 12/1996 | Klieman et al. |
| 5,590,778 A | 1/1997 | Dutchik |
| 5,592,065 A | 1/1997 | Oglesbee et al. |
| 5,597,531 A | 1/1997 | Liberti et al. |

(56) References Cited

U.S. PATENT DOCUMENTS

| | | |
|---|---|---|
| 5,599,350 A | 2/1997 | Schulze et al. |
| 5,630,420 A | 5/1997 | Vaitekunas |
| 5,630,456 A | 5/1997 | Hugo et al. |
| 5,690,222 A | 11/1997 | Peters |
| 5,707,369 A | 1/1998 | Vaitekunas et al. |
| 5,741,305 A | 4/1998 | Vincent et al. |
| 5,776,155 A | 7/1998 | Beaupre et al. |
| 5,800,336 A | 9/1998 | Ball et al. |
| 5,817,128 A | 10/1998 | Storz |
| 5,868,244 A | 2/1999 | Ivanov et al. |
| 5,871,493 A | 2/1999 | Sjostrom et al. |
| 5,873,873 A | 2/1999 | Smith et al. |
| 5,882,310 A | 3/1999 | Marian, Jr. |
| 5,893,835 A | 4/1999 | Witt et al. |
| 5,893,874 A | 4/1999 | Bourque et al. |
| 5,935,144 A * | 8/1999 | Estabrook ........ A61B 17/32006 604/22 |
| 5,938,633 A | 8/1999 | Beaupre |
| 5,944,737 A | 8/1999 | Tsonton et al. |
| 5,951,575 A | 9/1999 | Bolduc et al. |
| 5,980,510 A | 11/1999 | Tsonton et al. |
| 5,997,531 A | 12/1999 | Loeb et al. |
| 6,018,227 A | 1/2000 | Kumar et al. |
| 6,051,010 A | 4/2000 | Dimatteo et al. |
| 6,056,735 A | 5/2000 | Okada et al. |
| 6,063,098 A | 5/2000 | Houser et al. |
| 6,066,151 A | 5/2000 | Miyawaki et al. |
| 6,083,191 A | 7/2000 | Rose |
| 6,083,223 A | 7/2000 | Baker |
| 6,099,537 A | 8/2000 | Sugai et al. |
| 6,113,593 A | 9/2000 | Tu et al. |
| 6,123,702 A | 9/2000 | Swanson et al. |
| 6,165,191 A | 12/2000 | Shibata et al. |
| 6,190,386 B1 | 2/2001 | Rydell |
| 6,204,592 B1 | 3/2001 | Hur |
| 6,214,023 B1 | 4/2001 | Whipple et al. |
| 6,246,896 B1 | 6/2001 | Dumoulin et al. |
| 6,248,238 B1 | 6/2001 | Burtin et al. |
| 6,287,304 B1 | 9/2001 | Eggers et al. |
| 6,325,811 B1 | 12/2001 | Messerly |
| 6,339,368 B1 | 1/2002 | Leith |
| 6,398,755 B1 | 6/2002 | Belef et al. |
| 6,409,742 B1 | 6/2002 | Fulton, III et al. |
| 6,500,176 B1 | 12/2002 | Truckai et al. |
| 6,500,188 B2 | 12/2002 | Harper et al. |
| 6,512,667 B2 | 1/2003 | Shiue et al. |
| 6,514,267 B2 | 2/2003 | Jewett |
| 6,520,185 B1 | 2/2003 | Bommannan et al. |
| 6,561,983 B2 | 5/2003 | Cronin et al. |
| 6,562,032 B1 | 5/2003 | Ellman et al. |
| 6,609,414 B2 | 8/2003 | Mayer et al. |
| 6,622,731 B2 | 9/2003 | Daniel et al. |
| 6,623,500 B1 | 9/2003 | Cook et al. |
| 6,626,901 B1 | 9/2003 | Treat et al. |
| 6,647,281 B2 | 11/2003 | Morency |
| 6,650,091 B1 | 11/2003 | Shiue et al. |
| 6,650,975 B2 | 11/2003 | Ruffner |
| 6,656,177 B2 | 12/2003 | Truckai et al. |
| 6,658,301 B2 | 12/2003 | Loeb et al. |
| 6,666,875 B1 | 12/2003 | Sakurai et al. |
| 6,706,038 B2 | 3/2004 | Francishelli et al. |
| 6,717,193 B2 | 4/2004 | Olewine et al. |
| 6,730,042 B2 | 5/2004 | Fulton et al. |
| 6,753,673 B2 | 6/2004 | Shiue et al. |
| 6,758,855 B2 | 7/2004 | Fulton, III et al. |
| 6,761,698 B2 | 7/2004 | Shibata et al. |
| 6,761,701 B2 | 7/2004 | Cucin |
| 6,783,524 B2 | 8/2004 | Anderson et al. |
| 6,815,206 B2 | 11/2004 | Lin et al. |
| 6,821,671 B2 | 11/2004 | Hinton et al. |
| 6,836,097 B2 | 12/2004 | Turner et al. |
| 6,838,862 B2 | 1/2005 | Luu |
| 6,847,192 B2 | 1/2005 | Turner et al. |
| 6,860,880 B2 | 3/2005 | Treat et al. |
| 6,869,435 B2 | 3/2005 | Blake |
| 6,923,807 B2 | 8/2005 | Ryan et al. |
| 6,982,696 B1 | 1/2006 | Shahoian |
| 6,998,822 B2 | 2/2006 | Turner et al. |
| 7,031,155 B2 | 4/2006 | Sauciuc et al. |
| 7,061,749 B2 | 6/2006 | Liu et al. |
| 7,077,853 B2 | 7/2006 | Kramer et al. |
| 7,083,589 B2 | 8/2006 | Banko et al. |
| 7,085,123 B2 | 8/2006 | Shiue et al. |
| 7,101,371 B2 | 9/2006 | Dycus et al. |
| 7,112,201 B2 | 9/2006 | Truckai et al. |
| 7,125,409 B2 | 10/2006 | Truckai et al. |
| 7,150,712 B2 | 12/2006 | Buehlmann et al. |
| 7,169,146 B2 | 1/2007 | Truckai et al. |
| 7,186,253 B2 | 3/2007 | Truckai et al. |
| 7,186,473 B2 | 3/2007 | Shiue et al. |
| 7,189,233 B2 | 3/2007 | Truckai et al. |
| 7,220,951 B2 | 5/2007 | Truckai et al. |
| 7,221,216 B2 | 5/2007 | Nguyen |
| 7,232,440 B2 | 6/2007 | Dumbauld et al. |
| 7,244,024 B2 | 7/2007 | Biscardi |
| 7,292,227 B2 | 11/2007 | Fukumoto et al. |
| 7,296,804 B2 | 11/2007 | Lechot et al. |
| 7,303,556 B2 | 12/2007 | Metzger et al. |
| 7,309,849 B2 | 12/2007 | Truckai et al. |
| 7,311,709 B2 | 12/2007 | Truckai et al. |
| 7,349,741 B2 | 3/2008 | Maltan et al. |
| 7,354,440 B2 | 4/2008 | Truckai et al. |
| 7,364,061 B2 | 4/2008 | Swayze et al. |
| 7,364,554 B2 | 4/2008 | Bolze et al. |
| 7,381,209 B2 | 6/2008 | Truckai et al. |
| 7,416,101 B2 | 8/2008 | Shelton, IV et al. |
| 7,422,139 B2 | 8/2008 | Shelton, IV et al. |
| 7,464,846 B2 | 12/2008 | Shelton, IV et al. |
| 7,473,145 B2 | 1/2009 | Her et al. |
| 7,479,152 B2 | 1/2009 | Fulton, III et al. |
| 7,494,492 B2 | 2/2009 | Da Silva et al. |
| D594,983 S | 6/2009 | Price et al. |
| 7,560,903 B2 | 7/2009 | Thrap |
| 7,563,142 B1 | 7/2009 | Wenger et al. |
| 7,573,151 B2 | 8/2009 | Acena et al. |
| 7,583,564 B2 | 9/2009 | Ketahara et al. |
| 7,638,958 B2 | 12/2009 | Philipp et al. |
| 7,643,378 B2 | 1/2010 | Genosar |
| 7,658,247 B2 | 2/2010 | Carter |
| 7,692,411 B2 | 4/2010 | Trainor et al. |
| 7,717,312 B2 | 5/2010 | Beetel |
| 7,721,936 B2 | 5/2010 | Shelton, IV et al. |
| 7,738,971 B2 | 6/2010 | Swayze et al. |
| 7,761,198 B2 | 7/2010 | Bhardwaj |
| 7,766,910 B2 | 8/2010 | Hixson et al. |
| 7,766,929 B2 | 8/2010 | Masuda |
| 7,770,722 B2 | 8/2010 | Donahoe et al. |
| 7,770,775 B2 | 8/2010 | Shelton et al. |
| 7,776,037 B2 | 8/2010 | Odom |
| 7,780,660 B2 | 8/2010 | Bourne et al. |
| 7,802,121 B1 | 9/2010 | Zansky et al. |
| 7,815,658 B2 | 10/2010 | Murakami |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,862,579 B2 | 1/2011 | Ortiz et al. |
| 7,889,489 B2 | 2/2011 | Richardson et al. |
| 7,918,848 B2 | 4/2011 | Lau et al. |
| 7,923,151 B2 | 4/2011 | Lam et al. |
| 7,948,208 B2 | 5/2011 | Partovi et al. |
| 7,952,322 B2 | 5/2011 | Partovi et al. |
| 7,952,873 B2 | 5/2011 | Glahn et al. |
| 7,959,050 B2 | 6/2011 | Smith et al. |
| 7,977,921 B2 | 7/2011 | Bahai et al. |
| 7,982,439 B2 | 7/2011 | Trainor et al. |
| 8,038,025 B2 | 10/2011 | Stark et al. |
| 8,040,107 B2 | 10/2011 | Ishii |
| 8,052,605 B2 | 11/2011 | Muller et al. |
| 8,058,771 B2 | 11/2011 | Giordano et al. |
| 8,075,530 B2 | 12/2011 | Taylor et al. |
| 8,097,011 B2 | 1/2012 | Hideo et al. |
| 8,142,461 B2 | 3/2012 | Houser et al. |
| 8,147,488 B2 | 4/2012 | Masuda |
| 8,177,776 B2 | 5/2012 | Humayun et al. |

(56) References Cited

U.S. PATENT DOCUMENTS

| | | |
|---|---|---|
| 8,195,271 B2 | 6/2012 | Rahn |
| 8,210,411 B2 | 7/2012 | Yates et al. |
| 8,216,212 B2 | 7/2012 | Grant et al. |
| 8,221,418 B2 | 7/2012 | Prakash et al. |
| 8,240,498 B2 | 8/2012 | Ramsey et al. |
| 8,246,608 B2 | 8/2012 | Omori et al. |
| 8,246,642 B2 | 8/2012 | Houser et al. |
| 8,251,994 B2 | 8/2012 | McKenna et al. |
| 8,267,094 B2 | 9/2012 | Danek et al. |
| 8,277,446 B2 | 10/2012 | Heard |
| 8,292,882 B2 | 10/2012 | Danek et al. |
| 8,292,888 B2 | 10/2012 | Whitman |
| 8,298,253 B2 | 10/2012 | Charles |
| 8,301,262 B2 | 10/2012 | Mi et al. |
| 8,328,802 B2 | 12/2012 | Deville et al. |
| 8,333,764 B2 | 12/2012 | Francischelli et al. |
| 8,336,725 B2 | 12/2012 | Ramsey et al. |
| 8,337,097 B2 | 12/2012 | Cao |
| 8,344,690 B2 | 1/2013 | Smith et al. |
| 8,372,099 B2 | 2/2013 | Deville et al. |
| 8,377,059 B2 | 2/2013 | Deville et al. |
| 8,400,108 B2 | 3/2013 | Powell et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,419,757 B2 | 4/2013 | Smith et al. |
| 8,419,758 B2 | 4/2013 | Smith et al. |
| 8,425,545 B2 | 4/2013 | Smith et al. |
| 8,444,653 B2 | 5/2013 | Nycz et al. |
| 8,444,662 B2 | 5/2013 | Palmer et al. |
| 8,449,529 B2 | 5/2013 | Bek et al. |
| 8,461,744 B2 | 6/2013 | Wiener et al. |
| 8,487,487 B2 | 7/2013 | Dietz et al. |
| 8,550,106 B2 | 10/2013 | Hebach et al. |
| 8,550,981 B2 | 10/2013 | Woodruff et al. |
| 8,551,088 B2 | 10/2013 | Falkenstein et al. |
| 8,564,242 B2 | 10/2013 | Hansford et al. |
| 8,573,461 B2 | 11/2013 | Shelton et al. |
| 8,602,287 B2 | 12/2013 | Laurent et al. |
| 8,608,045 B2 | 12/2013 | Smith et al. |
| 8,617,077 B2 | 12/2013 | van Groningen et al. |
| 8,622,274 B2 | 1/2014 | Yates et al. |
| 8,623,027 B2 | 1/2014 | Price et al. |
| 8,632,535 B2 | 1/2014 | Shelton, IV et al. |
| 8,641,629 B2 | 2/2014 | Kurokawa |
| 8,657,174 B2 | 2/2014 | Yates et al. |
| 8,663,112 B2 | 3/2014 | Slayton et al. |
| 8,733,614 B2 | 5/2014 | Ross et al. |
| 8,758,342 B2 | 6/2014 | Bales et al. |
| 8,784,415 B2 | 7/2014 | Malackowski et al. |
| 8,808,319 B2 | 8/2014 | Houser et al. |
| 8,834,465 B2 | 9/2014 | Ramstein et al. |
| 8,864,761 B2 | 10/2014 | Johnson et al. |
| 8,906,017 B2 | 12/2014 | Rioux et al. |
| 8,939,974 B2 | 1/2015 | Boudreaux et al. |
| 8,961,441 B2 | 2/2015 | Cioanta et al. |
| 8,968,648 B2 | 3/2015 | Kaneko |
| 8,986,302 B2 | 3/2015 | Aldridge et al. |
| 8,998,939 B2 | 4/2015 | Price et al. |
| 9,000,720 B2 | 4/2015 | Stulen et al. |
| 9,011,336 B2 | 4/2015 | Slayton et al. |
| 9,011,427 B2 | 4/2015 | Price et al. |
| 9,011,471 B2 | 4/2015 | Timm et al. |
| 9,017,849 B2 | 4/2015 | Stulen et al. |
| 9,017,851 B2 | 4/2015 | Felder et al. |
| 9,023,071 B2 | 5/2015 | Miller et al. |
| 9,039,720 B2 | 5/2015 | Madan |
| 9,044,261 B2 | 6/2015 | Houser |
| 9,050,125 B2 | 6/2015 | Boudreaux et al. |
| 9,060,750 B2 | 6/2015 | Lam |
| 9,072,523 B2 | 7/2015 | Houser et al. |
| 9,072,543 B2 | 7/2015 | Miller et al. |
| 9,078,671 B2 | 7/2015 | Beale et al. |
| 9,089,338 B2 | 7/2015 | Smith et al. |
| 9,095,346 B2 | 8/2015 | Houser et al. |
| 9,113,903 B2 | 8/2015 | Unger |
| 9,161,803 B2 | 10/2015 | Yates et al. |
| 9,179,912 B2 | 11/2015 | Yates et al. |
| 9,186,046 B2 | 11/2015 | Ramamurthy et al. |
| 9,186,047 B2 | 11/2015 | Ramamurthy et al. |
| 9,192,428 B2 | 11/2015 | Houser et al. |
| 9,247,986 B2 | 2/2016 | Haberstich et al. |
| 9,308,009 B2 | 4/2016 | Madan et al. |
| 9,318,271 B2 | 4/2016 | Fletcher et al. |
| 9,364,279 B2 | 6/2016 | Houser et al. |
| 9,364,288 B2 | 6/2016 | Smith et al. |
| 9,375,255 B2 | 6/2016 | Houser et al. |
| 9,381,058 B2 | 7/2016 | Houser et al. |
| 9,421,062 B2 | 8/2016 | Houser et al. |
| 9,441,954 B2 | 9/2016 | Ramamurthy et al. |
| 9,500,472 B2 | 11/2016 | I Ramamurthy et al. |
| 9,500,473 B2 | 11/2016 | I Ramamurthy et al. |
| 9,510,895 B2 | 12/2016 | Houser et al. |
| 9,526,921 B2 | 12/2016 | Kimball et al. |
| 9,597,143 B2 | 3/2017 | Madan et al. |
| 9,616,803 B2 | 4/2017 | Jeong |
| 9,649,150 B2 | 5/2017 | Houser et al. |
| 9,782,214 B2 | 10/2017 | Houser et al. |
| 9,782,215 B2 | 10/2017 | Haberstich et al. |
| 10,085,792 B2 | 10/2018 | Johnson et al. |
| 10,143,513 B2 | 12/2018 | Houser et al. |
| 2001/0032666 A1 | 10/2001 | Jenson et al. |
| 2002/0165577 A1 | 11/2002 | Witt et al. |
| 2003/0093103 A1 | 5/2003 | Malackowski et al. |
| 2003/0109802 A1 | 6/2003 | Laeseke et al. |
| 2003/0114851 A1 | 6/2003 | Truckai et al. |
| 2003/0144680 A1 | 7/2003 | Kellogg et al. |
| 2004/0097911 A1 | 5/2004 | Murakami et al. |
| 2004/0116952 A1 | 6/2004 | Sakurai et al. |
| 2004/0133189 A1 | 7/2004 | Sakurai |
| 2004/0173487 A1 | 9/2004 | Johnson et al. |
| 2005/0021065 A1 | 1/2005 | Yamada et al. |
| 2005/0033195 A1 | 2/2005 | Fulton, III et al. |
| 2005/0171522 A1 | 8/2005 | Christopherson |
| 2005/0203546 A1 | 9/2005 | Van Wyk et al. |
| 2006/0030797 A1 | 2/2006 | Zhou et al. |
| 2006/0079829 A1 | 4/2006 | Fulton, III et al. |
| 2006/0079874 A1 | 4/2006 | Faller et al. |
| 2006/0079877 A1 | 4/2006 | Houser et al. |
| 2006/0079879 A1 | 4/2006 | Faller et al. |
| 2006/0253176 A1 | 11/2006 | Caruso et al. |
| 2007/0027447 A1 | 2/2007 | Theroux et al. |
| 2007/0103437 A1 | 5/2007 | Rosenberg |
| 2007/0191713 A1 | 8/2007 | Eichmann et al. |
| 2007/0207354 A1 | 9/2007 | Curello et al. |
| 2007/0261978 A1 | 11/2007 | Sanderson |
| 2007/0265613 A1 | 11/2007 | Edelstein |
| 2007/0265620 A1 | 11/2007 | Kraas et al. |
| 2007/0282333 A1 | 12/2007 | Fortson et al. |
| 2008/0003491 A1 | 1/2008 | Yahnker et al. |
| 2008/0004656 A1 | 1/2008 | Livneh |
| 2008/0057470 A1 | 3/2008 | Levy et al. |
| 2008/0147058 A1 | 6/2008 | Horrell et al. |
| 2008/0150754 A1 | 6/2008 | Quendt |
| 2008/0173651 A1 | 7/2008 | Ping |
| 2008/0188810 A1 | 8/2008 | Larsen et al. |
| 2008/0200940 A1 | 8/2008 | Eichmann et al. |
| 2008/0228104 A1 | 9/2008 | Uber, III et al. |
| 2008/0255413 A1 | 10/2008 | Zemlok et al. |
| 2008/0281301 A1 | 11/2008 | Deboer et al. |
| 2008/0315829 A1 | 12/2008 | Jones et al. |
| 2009/0043797 A1 | 2/2009 | Dorie et al. |
| 2009/0076506 A1 | 3/2009 | Baker |
| 2009/0096430 A1 | 4/2009 | Van Der Linde et al. |
| 2009/0143799 A1 | 6/2009 | Smith et al. |
| 2009/0143800 A1 | 6/2009 | Deville et al. |
| 2009/0253030 A1 | 10/2009 | Kooij |
| 2009/0281430 A1 | 11/2009 | Wilder |
| 2010/0021022 A1 | 1/2010 | Pittel et al. |
| 2010/0030218 A1 | 2/2010 | Prevost |
| 2010/0060231 A1 | 3/2010 | Trainor et al. |
| 2010/0076455 A1 | 3/2010 | Birkenbach et al. |
| 2010/0106144 A1 | 4/2010 | Matsumura et al. |
| 2010/0106146 A1 | 4/2010 | Boitor et al. |

(56) References Cited

U.S. PATENT DOCUMENTS

| | | |
|---|---|---|
| 2010/0125172 A1 | 5/2010 | Jayaraj |
| 2010/0152610 A1 | 6/2010 | Parihar et al. |
| 2010/0201311 A1 | 8/2010 | Alexander et al. |
| 2010/0249665 A1 | 9/2010 | Roche |
| 2010/0268221 A1 | 10/2010 | Beller et al. |
| 2010/0274160 A1 | 10/2010 | Yachi et al. |
| 2011/0009694 A1 | 1/2011 | Schultz et al. |
| 2011/0074336 A1 | 3/2011 | Miller |
| 2011/0077514 A1 | 3/2011 | Ulric et al. |
| 2011/0080134 A1 | 4/2011 | Miller |
| 2011/0221398 A1 | 9/2011 | Ferber |
| 2012/0111591 A1 | 5/2012 | Shelton, IV et al. |
| 2012/0116260 A1 | 5/2012 | Johnson et al. |
| 2012/0116261 A1 | 5/2012 | Mumaw et al. |
| 2012/0116262 A1 | 5/2012 | Houser et al. |
| 2012/0116263 A1 | 5/2012 | Houser et al. |
| 2012/0116265 A1 | 5/2012 | Houser et al. |
| 2012/0116266 A1 | 5/2012 | Houser et al. |
| 2012/0116366 A1 | 5/2012 | Houser et al. |
| 2012/0116380 A1 | 5/2012 | Madan et al. |
| 2012/0116381 A1 | 5/2012 | Houser et al. |
| 2012/0116391 A1 | 5/2012 | Houser et al. |
| 2012/0179036 A1 | 7/2012 | Patrick et al. |
| 2012/0292367 A1 | 11/2012 | Morgan et al. |
| 2012/0305427 A1 | 12/2012 | Felder et al. |
| 2013/0085330 A1 | 4/2013 | Ramamurthy et al. |
| 2013/0090528 A1 | 4/2013 | Ramamurthy et al. |
| 2013/0090675 A1 | 4/2013 | Mumaw et al. |
| 2013/0118733 A1 | 5/2013 | Kumar |
| 2014/0088379 A1 | 3/2014 | Bhamra et al. |
| 2016/0121143 A1 | 5/2016 | Mumaw et al. |
| 2016/0206900 A1 | 7/2016 | Haberstich et al. |
| 2016/0329614 A1 | 11/2016 | Madan et al. |
| 2016/0338760 A1 | 11/2016 | Houser et al. |

FOREIGN PATENT DOCUMENTS

| | | |
|---|---|---|
| EP | 0897696 A1 | 2/1999 |
| EP | 0947167 A1 | 10/1999 |
| EP | 1330991 A1 | 7/2003 |
| EP | 1525853 A2 | 4/2005 |
| EP | 1535585 A2 | 6/2005 |
| EP | 1684396 A2 | 7/2006 |
| EP | 1721576 A1 | 11/2006 |
| EP | 1743592 A1 | 1/2007 |
| EP | 1818021 A1 | 8/2007 |
| EP | 1839599 | 10/2007 |
| EP | 1868275 A2 | 12/2007 |
| EP | 1886637 A1 | 2/2008 |
| EP | 1263341 B1 | 6/2008 |
| EP | 1943976 A2 | 7/2008 |
| EP | 1970014 | 9/2008 |
| EP | 1997439 A2 | 12/2008 |
| EP | 2027819 A1 | 2/2009 |
| EP | 2090256 A2 | 8/2009 |
| EP | 2105104 A2 | 9/2009 |
| EP | 2165660 A2 | 3/2010 |
| EP | 2218409 A1 | 8/2010 |
| EP | 2243439 A1 | 10/2010 |
| EP | 2345454 A1 | 7/2011 |
| GB | 2425874 | 11/2006 |
| GB | 2440566 A | 2/2008 |
| JP | H 10-118090 A | 5/1998 |
| JP | 2002-186627 A | 7/2002 |
| JP | 4602681 | 10/2005 |
| JP | 4836148 | 4/2010 |
| WO | WO 1997/024072 | 7/1997 |
| WO | WO 2000/065682 | 2/2000 |
| WO | WO 2003/013374 | 2/2003 |
| WO | WO 2003/020139 | 3/2003 |
| WO | WO 2004/113991 | 12/2004 |
| WO | WO 2005/079915 | 9/2005 |
| WO | WO 2006/023266 | 3/2006 |
| WO | WO 2007/004515 | 1/2007 |
| WO | WO 2007/024983 | 3/2007 |
| WO | WO 2007/090025 | 8/2007 |
| WO | WO 2007/137115 | 11/2007 |
| WO | WO 2007/137304 | 11/2007 |
| WO | WO 2008/071898 | 6/2008 |
| WO | WO 2008/102154 | 8/2008 |
| WO | WO 2008/107902 | 9/2008 |
| WO | WO 2008/131357 | 10/2008 |
| WO | WO 2009/018409 | 2/2009 |
| WO | WO 2009/046394 | 4/2009 |
| WO | WO 2009/070780 | 6/2009 |
| WO | WO 2009/073608 | 6/2009 |
| WO | WO 2010/030850 | 3/2010 |
| WO | WO 2010/096174 | 8/2010 |
| WO | WO 2011/059785 | 5/2011 |
| WO | WO 2011/089270 | 7/2011 |

OTHER PUBLICATIONS

"System 6 Aseptic Battery System," Stryker (2006) pp. 1-2.
EP Communication dated Feb. 19, 2014 for Application No. EP 11781972.2.
International Search Report and Written Opinion dated Jan. 26, 2012 for Application No. PCT/US2011/059212.
International Preliminary Report on Patentability dated May 7, 2013 for Application No. PCT/US2011/059212.
Communication from International Searching Authority dated Jan. 24, 2012 tor Application No. PCT/US2011/059215.
International Search Report dated Apr. 4, 2012 for Application No. PCT/US2011/059215.
International Preliminary Report on Patentability dated May 8, 2013 for Application No. PCT/US2011/059215.
International Search Report dated Feb. 13, 2012for Application No. PCT/US2011/059217.
International Preliminary Report on Patentability dated May 7, 2013 for Application No. PCT/US2011/0592717.
International Search Report dated Jun. 12, 2012 for Application No. PCT/US2011/059218.
International Preliminary Report on Patentability dated May 7, 2013 for Application No. PCY/US2011/059218.
International Search Report dated Jan. 26, 2012 for Application No. PCT/US11/059220.
International Preliminary Report on Patentability dated May 7, 2013 for Application No. PCT/US2011/059220.
Communication from International Searching Authority dated Feb. 2, 2012for Application No. PCT/US2011/059222.
International Search Report dated Apr. 18, 2012 for Application No. PCT/US2011/059222.
International Preliminary Report on Patentability dated May. 7, 2013 for Application No. PCT/US2011/059222.
Internatlonal Search Report dated Feb. 1, 2012 for Application No. PCT/US11/059223.
International Preliminary Report on Patentability dated May 7, 2013 for Application No. PCT/US2011/059223.
International Search Report dated Jan. 12, 2012 for Application No. PCT/US11/059226.
International Preliminary Report on Patentability dated May 7, 2013 for Application No. PCT/US2011/059226.
International Search Report dated Mar. 15, 2012 for Application No. PCT/US2011/059338.
International Preliminary Report on Patentability dated May 7, 2013 for Application No. PCT/US2011/059338.
International Search Report dated Feb. 7, 2012 for Applcation No. PCT/US2011/059351.
International Preliminary Report on Patentability dated May 7, 2013 for Application No. PCT/US2011/059351.
International Search Report dated Feb. 2, 2012for Application No. PCT/US2011/059354.
International Preliminary Report on Patentability dated May 7, 2013 for Application No. PCT/US2011/059354.
International Search Report dated May 29, 2012 for Application No. PCT/US11/059358.
International Preliminary Report on Patentability dated May 7, 2013 for Application No. PCT/US2011/059358.

(56) References Cited

OTHER PUBLICATIONS

Communication from International Searching Authority dated Feb. 6, 2012 for Application No. PCT/US2011/059362.
International Search Report dated Mar. 22, 2012 for Application No. PCT/US2011/059362.
International Preliminary Report on Patentability dated May 7, 2013 for Application No. PCT/US2011/059362.
International Search Report dated Jun. 4, 2012 for Application No. PCT/US2011/059365.
International Preliminary Report on Patentability dated May 8, 2013 for Application No. PCT/US2011/059365.
International Search Report dated Feb. 23, 2012 for Application No. PCT/US2011/059371.
International Preliminary Report on Patentability dated May 7, 2013 for Application No. PCT/US2011/059371.
Communication from International Searching Authority dated Feb. 2, 2012 for Application No. PCT/US2011/059378.
International Search Report dated May 24, 2012 for Application No. PCT/US2011/059378.
International Search Report and Written Opinion dated Feb. 2, 2012 for Application No. PCT/US2011/059378.
International Preliminary Report on Patentability dated May 7, 2013 for Application No. PCT/US2011/059378.
International Search Report dated Apr. 11, 2012 for Application No. PCT/US2011/059381.
International Search Report and Written Opinion dated Jul. 6, 2012 for PCT/US2011/059381.
International Preliminary Report on Patentability dated May 8, 2013 for Application No. PCT/US2011/059381.
Office Action Non-Final dated Aug. 6, 2013 for U.S. Appl. No. 13/151,471.
Notice of Allowance dated Dec. 6, 2013 for U.S. Appl. No. 13/151,471.
Office Action Non-Final dated Mar. 28, 2014 for U.S. Appl. No. 13/151,471.
U.S. Office Action, Notice of Allowance, dated Aug. 19, 2014 for U.S. Appl. No. 13/151,471.
U.S. Office Action, Notice of Allowance, dated Nov. 21, 2014 for U.S. Appl. No. 13/151,471.
Restriction Requirement dated Dec. 11, 2012 for U.S. Appl. No. 13/151,481.
Office Action Non-Final dated Feb. 15, 2013 for U.S. Appl. No. 13/151,481.
Office Action Final dated Jun. 7, 2013 for U.S. Appl. No. 13/151,481.
U.S. Office Action, Non-Final, dated Aug. 14, 2014 for U.S. Appl. No. 13/151,481.
Restriction Requirement dated Jul. 5, 2013 for U.S. Appl. No. 13/151,488.
U.S. Office Action, Non-Final, dated Nov. 7, 2014 for U.S. Appl. No. 13/151,488.
Office Action Non-Final dated Jun. 14, 2013 for U.S. Appl. No. 13/151,498.
Office Action Final dated Nov. 21, 2013 for U.S. Appl. No. 13/151,498.
Office Action Non Final dated Mar. 18, 2014 for U.S. Appl. No. 13/151,498.
U.S. Office Action, Notice of Allowance, dated Aug. 6, 2014 for U.S. Appl. No. 13/151,498.
U.S. Office Action, Notice of Allowance, dated Nov. 21, 2014 for U.S. Appl. No. 13/151,498.
Office Action Non Final dated Jun. 18, 2014 for U.S. Appl. No. 13/151,503.
Office Action Non Final dated Nov. 6, 2014 for U.S. Appl. No. 13/151,503.
Restriction Requirement dated Mar. 13, 2013 for U.S. Appl. No. 13/151,509.
Restriction Requirement dated Jun. 24, 2013 for U.S. Appl. No. 13/151,509.
Office Action Non-Final dated Sep. 26, 2013 for U.S. Appl. No. 13/151,509.
Office Action Final dated Jan. 29, 2014 for U.S. Appl. No. 13/151,509.
Office Action Non-Final dated Jul. 9, 2014 for U.S. Appl. No. 13/151,509.
U.S. Office Action, Notice of Allowance, dated Oct. 28, 2014 for U.S. Appl. No. 13/151,509.
Restriction Requirement dated Jun. 11, 2014 for U.S. Appl. No. 13/151,512.
U.S. Office Action, Notice of Allowance, date Oct. 29, 2014 for U.S. Appl. No. 13/151,512.
U.S. Office Action, Restriction Requirement, dated Jul. 11, 2014 for U.S. Appl. No. 13/269,870.
Restriction Requirement dated Feb. 28, 2013 for U.S. Appl. No. 13/270,667.
Office Action Non-Final dated Apr. 26, 2013 for U.S. Appl. No. 13/270,667.
Office Action Final dated Oct. 25, 2013 for U.S. Appl. No. 13/270,667.
U.S. Office Action, Non-Final, dated Jul. 29, 2014 for U.S. Appl. No. 13/270,667.
U.S. Office Action, Restriction Requirement, dated Jul. 9, 2014 for U.S. Appl. No. 13/270,684.
U.S. Office Action, Non-Final, dated Oct. 9, 2014 for U.S. Appl. No. 13/270,684.
U.S. Office Action, Restriction Requirement, dated Sep. 11, 2014 for U.S. Appl. No. 13/270,701.
Office Action Non-Final dated Nov. 21, 2013 for U.S. Appl. No. 13/271,352.
U.S. Office Action, Restriction Requirement, dated Sep. 25, 2014 for U.S. Appl. No. 13/271,352.
U.S. Office Action, Restriction Requirement, dated Oct. 2, 2013 for U.S. Appl. No. 13/274,480.
Office Action Non-Final dated Feb. 14, 2014 for U.S. Appl. No. 13/274,480.
U.S. Office Action, Final, dated Jul. 17, 2014 for U.S. Appl. No. 13/274,480.
Restriction Requirement dated Mar. 28, 2014 for U.S. Appl. No. 13/274,507.
Office Action Non-Final dated Jun. 19, 2014 for U.S. Appl. No. 13/274,507.
Office Action Non-Final dated Dec. 21, 2012 for U.S. Appl. No. 13/274,516.
Office Action Final dated Aug. 16, 2013 for U.S. Appl. No. 13/274,516.
Office Action Non-Final dated Dec. 6, 2013 for U.S. Appl. No. 13/274,516.
U.S. Office Action, Final, dated Jun. 12, 2012 for U.S. Appl. No. 13/274,516.
U.S. Office Action, Non-Final, dated Oct. 8, 2014 for U.S. Appl. No. 13/274,516.
Restriction Requirement dated Feb. 25, 2013 for U.S. Appl. No. 13/274,540.
Office Action Non-Final dated Apr. 30, 2013 for U.S. Appl. No. 13/274,540.
Office Action Final dated Oct. 25, 2013 for U.S. Appl. No. 13/274,540.
U.S. Office Action, Non-Final, dated Aug. 26, 2014 for U.S. Appl. No. 13/274,540.
Office Action Non-Final dated Apr. 1, 2013 for U.S. Appl. No. 13/274,805.
Office Action Final dated Sep. 12, 2013 for U.S. Appl. No. 13/274,805.
U.S. Office Action, Non-Final, dated Aug. 14, 2014 for U.S. Appl. No. 13/274,805.
Restriction Requirement dated Apr. 29, 2013 for U.S. Appl. No. 13/274,830.
Office Action Non-Final dated Jun. 14, 2013 for U.S. Appl. No. 13/274,830.
Office Action Final dated Nov. 26, 2013 for U.S. Appl. No. 13/274,830.
U.S. Office Action, Non-Final, dated Oct. 22, 2014 for U.S. Appl. No. 13/274,830.
Restriction Requirement dated Apr. 4, 2013 for U.S. Appl. No. 13/275,495.
Office Action Non-Final dated May 31, 2013 for U.S. Appl. No. 13/275,495.
Office Action Final dated Dec. 5, 2013 for U.S. Appl. No. 13/275,495.

(56) References Cited

OTHER PUBLICATIONS

Office Action Non-Final dated Jan. 6, 2014 for U.S. Appl. No. 13/275,514.
U.S. Office Action, Non-Final, dated Sep. 9, 2014 for U.S. Appl. No. 13/275,514.
Office Action Non-Final dated May 17, 2013 for U.S. Appl. No. 13/275,547.
Office Action Final dated Feb. 28, 2014 for U.S. Appl. No. 13/275,547.
U.S. Office Action, Non-Final, dated Aug. 20, 2014 for U.S. Appl. No. 13/275,547.
Office Action Non-Final dated Feb. 1, 2013 for U.S. Appl. No. 13/275,563.
Office Action Final dated Aug. 29, 2013 for U.S. Appl. No. 13/275,563.
U.S. Office Action, Non-Final, dated Oct. 23, 2014 for U.S. Appl. No. 13/275,563.
Restriction Requirement dated Feb. 6, 2013 for U.S. Appl. No. 13/276,660.
Office Action Non-Final dated Jun. 3, 2013 for U.S. Appl. No. 13/246,660.
U.S. Office Action, Restriction Requirement, dated Jul. 9, 2014 for U.S. Appl. No. 13/276,660.
Office Action Non-Final dated Dec. 21, 2012 for U.S. Appl. No. 13/276,673.
Office Action Non-Final dated Aug. 19, 2013 for U.S. Appl. No. 13/276,673.
Office Action Final dated Mar. 21, 2014 for U.S. Appl. No. 13/276,673.
U.S. Office Action, Non-Final, dated Aug. 14, 2014 for U.S. Appl. No. 13/276,673.
Restriction Requirement dated Feb. 6, 2013 for U.S. Appl. No. 13/276,687.
Office Action Non-Final dated Jun. 12, 2013 for U.S. Appl. No. 13/276,687.
Notice of Allowance dated Nov. 12, 2013 for U.S. Appl. No. 13/276,687.
Notice of Allowance dated Jun. 2, 2014 for U.S. Appl. No. 13/276,687.
U.S. Office Action, Notice of Allowance, dated Sep. 12, 2014 for U.S. Appl. No. 13/276,687.
Restriction Requirement dated Feb. 21, 2013 for U.S. Appl. No. 13/276,707.
Office Action Non-Final dated May 6, 2013 for U.S. Appl. No. 13/276,707.
Office Action Final dated Sep. 27, 2013 for U.S. Appl. No. 13/276,707.
Restriction Requirement dated Feb. 6, 2013 for U.S. Appl. No. 13/276,725.
U.S. Office Action, Non-Final, dated Aug. 20, 2014 for U.S. Appl. No. 13/276,725.
Restriction Requirement dated Dec. 21, 2012 for U.S. Appl. No. 13/276,745.
Office Action Non-Final dated Apr. 30, 2013 for U.S. Appl. No. 13/276,745.
Office Action Final dated Nov. 8, 2013 for U.S. Appl. No. 13/276,745.
Office Action Non-Final dated Feb. 28, 2014 for U.S. Appl. No. 13/276,745.
U.S. Office Action, Notice of Allowance, dated Oct. 7, 2014 for U.S. Appl. No. 13/276,745.
U.S. Office Action, Restriction Requirement, dated Sep. 24, 2014 for U.S. Appl. No. 13/277,328.
Australian Firrt Examination Report dated Jun. 11, 2015 for App. No. 2011323281.
Chinese First Office Action dated Apr. 16, 2015 for App. No. CN 201180063919X.
Chinese First Office Action dated Jun. 1, 2015 for App. No. CN 2011800640981.
Japanese Office Action, Notification of Reasons for Refusal, dated Sep. 8, 2015 for App. No. 2013-537830.
Japanese Office Action, Notification of Reasons for Refusal, dated Aug. 25, 2015 for App. No. 2013-537831.
U.S. Office Action, Non-Final, dated Apr. 1, 2015 for U.S. Appl. No. 13/151,481.
U.S. Office Action, Notice of Allowance, dated Feb. 25, 2015 for U.S. Appl. No. 13/151,509.
U.S. Office Action, Notice of Allowance, dated Feb. 17, 2015 for U.S. Appl. No. 13/151,512.
U.S. Office Action, Non-Final, dated Jan. 5, 2015 for U.S. Appl. No. 13/269,870.
U.S. Office Action, Final, dated Aug. 14, 2015 for U.S. Appl. No. 13/269,870.
U.S. Office Action, Notice of Allowance, dated Apr. 4, 2016 for U.S. Appl. No. 13/269,870.
U.S. Office Action, Notice of Allowance, dated Jul. 27, 2016 for U.S. Appl. No. 13/269,870.
U.S. Office Action, Notice of Allowance, dated Dec. 17, 2014 for U.S. Appl. No. 13/270,667.
U.S. Office Action, Final, dated Mar. 17, 2015 for U.S. Appl. No. 13/270,684.
U.S. Office Action, Notice of Allowance, dated Jul. 28, 2015 for U.S. Appl. No. 13/270,684.
U.S. Office Action, Notice of Allowance, dated Nov. 30, 2015 for U.S. Appl. No. 13/270,684.
U.S. Office Action, Non-Final, dated Dec. 16, 2014 for U.S. Appl. No. 13/270,701.
U.S. Office Action, Non-Final, dated Mar. 26, 2015 for U.S. Appl. No. 13/271,352.
U.S. Office Action, Final, dated Jul. 15, 2015 for U.S. Appl. No. 13/271,352.
U.S. Office Action, Notice of Allowance, dated Feb. 19, 2016 for U.S. Appl. No. 13/271,352.
U.S. Office Action, Non-Final, dated Jul. 14, 2015 for U.S. Appl. No. 13/271,364.
U.S. Office Action, Notice of Allowance, dated Dec. 18, 2015 for U.S. Appl. No. 13/271,364.
U.S. Office Action, Notice of Allowance, dated Apr. 7, 2016 for U.S. Appl. No. 13/271,364.
U.S. Office Action, Restriction Requirement, dated Dec. 9, 2013 for U.S. Appl. No. 13/274,496.
U.S. Office Action, Non-Final, dated Feb. 6, 2014 for U.S. Appl. No. 13/274,496.
U.S. Office Action, Final, dated May 15, 2014 for U.S. Appl. No. 13/274,496.
U.S. Office Action, Final, dated Aug. 22, 2014 for U.S. Appl. No. 13/274,496.
U.S. Office Action, Non-Final, dated Apr. 2, 2015 for U.S. Appl. No. 13/274,496.
U.S. Office Action, Non-Final, dated Jul. 22, 2015 for U.S. Appl. No. 13/274,507.
U.S. Office Action, Final, dated Dec. 8, 2015 for U.S. Appl. No. 13/274,507.
U.S. Office Action, Final, dated May 8, 2015 for U.S. Appl. No. 13/274,516.
U.S. Office Action, Notice of Allowance, dated Sep. 24, 2015 for U.S. Appl. No. 13/274,516.
U.S. Office Action, Notice of Allowance, dated Jan. 21, 2015 for U.S. Appl. No. 13/274,540.
U.S. Office Action, Notice of Allowance, dated Nov. 28, 2014 for U.S. Appl. No. 13/274,805.
U.S. Office Action, Notice of Allowance, dated Jan. 21, 2015 for U.S. Appl. No. 13/274,805.
U.S. Office Action, Notice of Allowance, dated Mar. 23, 2015 for U.S. Appl. No. 13/274,830.
U.S. Office Action, Non-Final, dated Feb. 25, 2015 for U.S. Appl. No. 13/275,495.
U.S. Office Action, Final, dated Mar. 10, 2015 for U.S. Appl. No. 13/275,547.
U.S. Office Action, Final, dated Mar. 13, 2015 for U.S. Appl. No. 13/276,673.
U.S. Office Action, Notice of Allowance, dated Dec. 23, 2014 for U.S. Appl. No. 13/276,687.
U.S. Office Action, Non-Final, dated Jan. 29, 2015 for U.S. Appl. No. 13/276,707.

(56) References Cited

OTHER PUBLICATIONS

U.S. Office Action, Notice of Allowance, dated Mar. 13, 2015 for U.S. Appl. No. 13/276,725.
U.S. Office Action, Notice of Allowance, dated Dec. 19, 2014 for U.S. Appl. No. 13/276,745.
U.S. Office Action, Non-Final, dated Dec. 8, 2014 for U.S. Appl. No. 13/277,328.
U.S. Office Action, Final, dated Mar. 24, 2015 for U.S. Appl. No. 13/277,328.
U.S. Office Action, Notice of Allowance, dated Jun. 1, 2015 for U.S. Appl. No. 13/277,328.
U.S. Office Action, Non-Final, dated Aug. 26, 2016 for U.S. Appl. No. 15/008,530.
U.S. Office Action, Notice of Allowance, dated May 17, 2018 for U.S. Appl. No. 13/270,701.
U.S. Office Action, Notice of Allowance, dated Jul. 23, 2018 for U.S. Appl. No. 13/274,507, 5 pgs.
U.S. Office Action, Restriction Requirement, dated Jun. 14, 2018 for U.S. Appl. No. 15/342,218, 6 pgs.
U.S. Office Action, Non-Final, dated Nov. 19, 2018 for U.S. Appl. No. 15/342,218, 6 pgs.
U.S. Office Action, Notice of Allowance, dated Feb. 1, 2017 for U.S. Appl. No. 15/008,530.
U.S. Office Action, Notice of Allowance, dated Jun. 16, 2017 for U.S. Appl. No. 15/008,530.
U.S. Appl. No. 13/151,488.
U.S. Appl. No. 13/274,480.
U.S. Appl. No. 13/274,496.
U.S. Appl. No. 13/275,495.
U.S. Appl. No. 13/275,547.
U.S. Appl. No. 13/275,563.
U.S. Appl. No. 14/992,104.
U.S. Appl. No. 15/212,423.
U.S. Appl. No. 15/229,418.
U.S. Appl. No. 15/342,218.
Japanese Office Action, Notification of Reasons for Refusal, dated Jan. 9, 2018 for Application No. JP 2013-537835, Trial against Examiner's Decision of Refusal No. JP 2016-19055, 7 pgs.
U.S. Appl. No. 15/460,822.
U.S. Appl. No. 15/695,151.
U.S. Appl. No. 16/530,009.
U.S. Pat. No. 10,376,304.
European Examination Report dated May 18, 2018 for Application No. EP 11784882.0, 4 pgs.
Indian Office Action, Examination Report, dated Sep. 25, 2019 for Application No. 3969/DELNP/2013, 8 pgs.
Indian Office Action, Examination Report, dated Aug. 7, 2019 for Application No. 3971/DELNP/2013, 8 pgs.
Indian Office Action, Examination Report, dated Aug. 16, 2019 for Application No. 3972/DELNP/2013, 5 pgs.
Indian Office Action, Examination Report, dated Nov. 15, 2019 for Application No. 3967/DELNP/2013, 6 pgs.
Indian Office Action, Examination Report, dated Dec. 5, 2019 for Application No. 3974/DELNP/2013, 8 pgs.
U.S. Appl. No. 61/410,603, filed Nov. 5, 2010, by Houser, entitled: "Energy-Based Surgical Instruments".
U.S. Appl. No. 61/487,846, filed May 19, 2011, by Boudreaux et al., entitled: "Ultrasonic Surgical Instruments".

\* cited by examiner

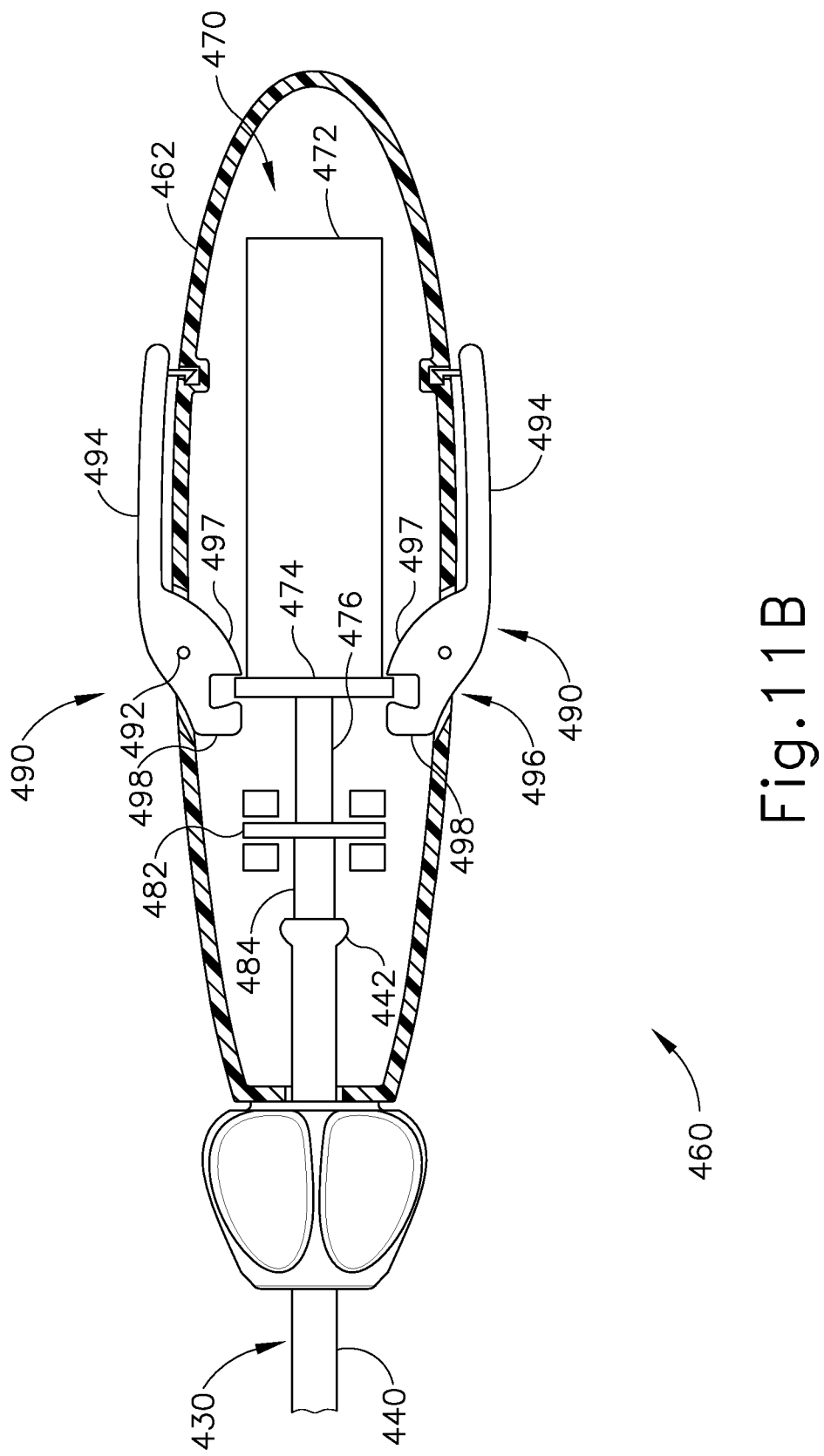

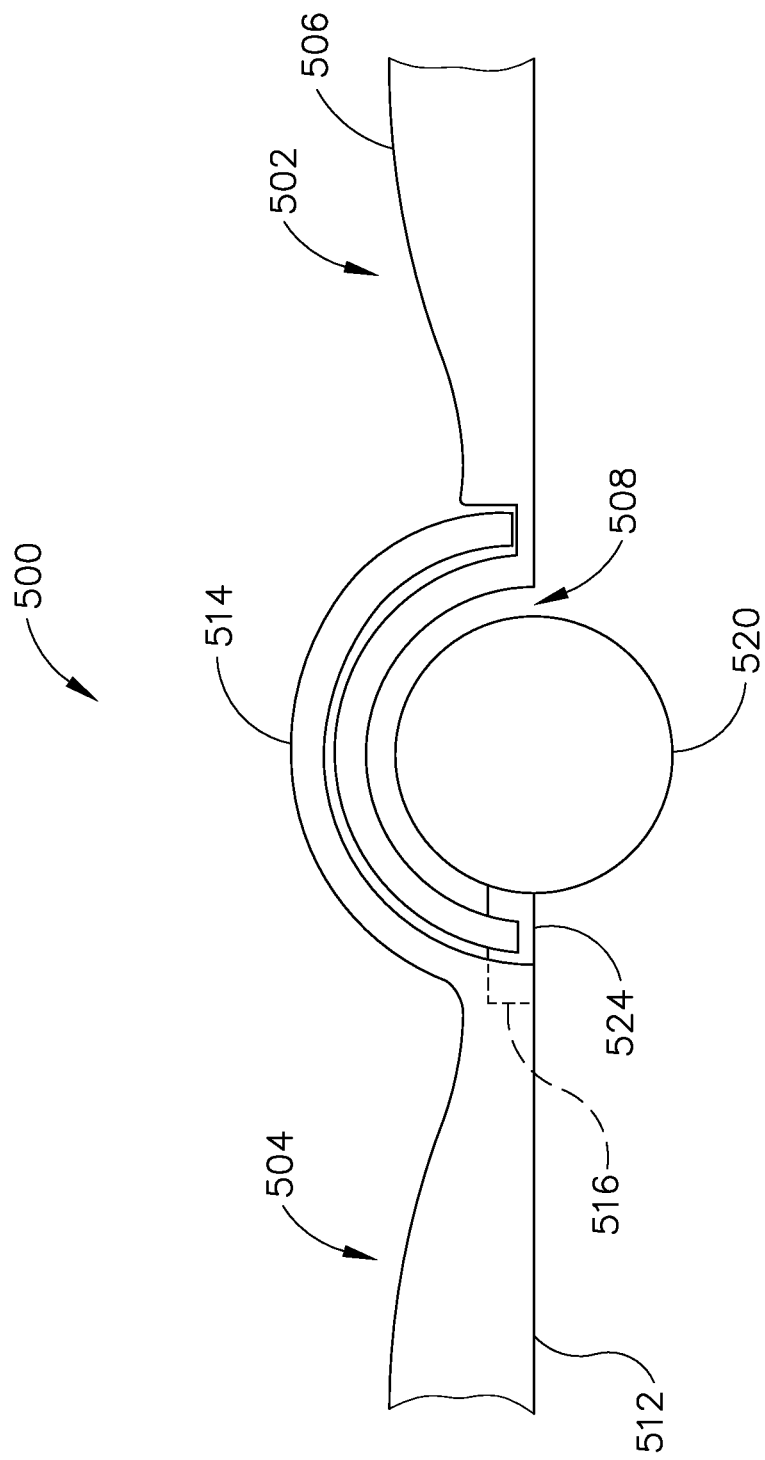

US 10,881,448 B2

CAM DRIVEN COUPLING BETWEEN ULTRASONIC TRANSDUCER AND WAVEGUIDE IN SURGICAL INSTRUMENT

PRIORITY

This application is a divisional application of U.S. application Ser. No. 13/274,496, filed on Oct. 17, 2011, published as U.S. Pub. No. 2012/0116262 on May 10, 2012, now abandoned, which claims the benefit of U.S. Provisional Application Ser. No. 61/410,603, filed Nov. 5, 2010, entitled "Energy-Based Surgical Instruments," the disclosure of which is incorporated by reference herein.

This application also claims the benefit of U.S. Provisional Application Ser. No. 61/487,846, filed May 19, 2011, entitled "Ultrasonic Surgical Instruments," the disclosure of which is incorporated by reference herein.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient.

Examples of endoscopic surgical instruments include those disclosed in U.S. Pat. Pub. No. 2006/0079874, entitled "Tissue Pad for Use with an Ultrasonic Surgical Instrument," published Apr. 13, 2006, now abandoned, the disclosure of which is incorporated by reference herein; U.S. Pat. Pub. No. 2007/0191713, entitled "Ultrasonic Device for Cutting and Coagulating," published Aug. 16, 2007, now abandoned, the disclosure of which is incorporated by reference herein; U.S. Pat. Pub. No. 2007/0282333, entitled "Ultrasonic Waveguide and Blade," published Dec. 6, 2007, now abandoned, the disclosure of which is incorporated by reference herein; U.S. Pat. Pub. No. 2008/0200940, entitled "Ultrasonic Device for Cutting and Coagulating," published Aug. 21, 2008, now abandoned, the disclosure of which is incorporated by reference herein; U.S. Pat. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; and U.S. Pat. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein. Additionally, such surgical tools may include a cordless transducer such as that disclosed in U.S. Pat. Pub. No. 2009/0143797, entitled "Cordless Hand-held Ultrasonic Cautery Cutting Device," published Jun. 4, 2009, issued as U.S. Pat. No. 8,419,757 on Apr. 16, 2013, the disclosure of which is incorporated by reference herein. In addition, the surgical instruments may be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

While several systems and methods have been made and used for surgical instruments, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 11B depicts a top view of the instrument of FIG. 11A showing the transducer unit in a locked position;

FIG. 14 depicts a rear view of the clamshell handle assembly of FIG. 12.

Figure 1:
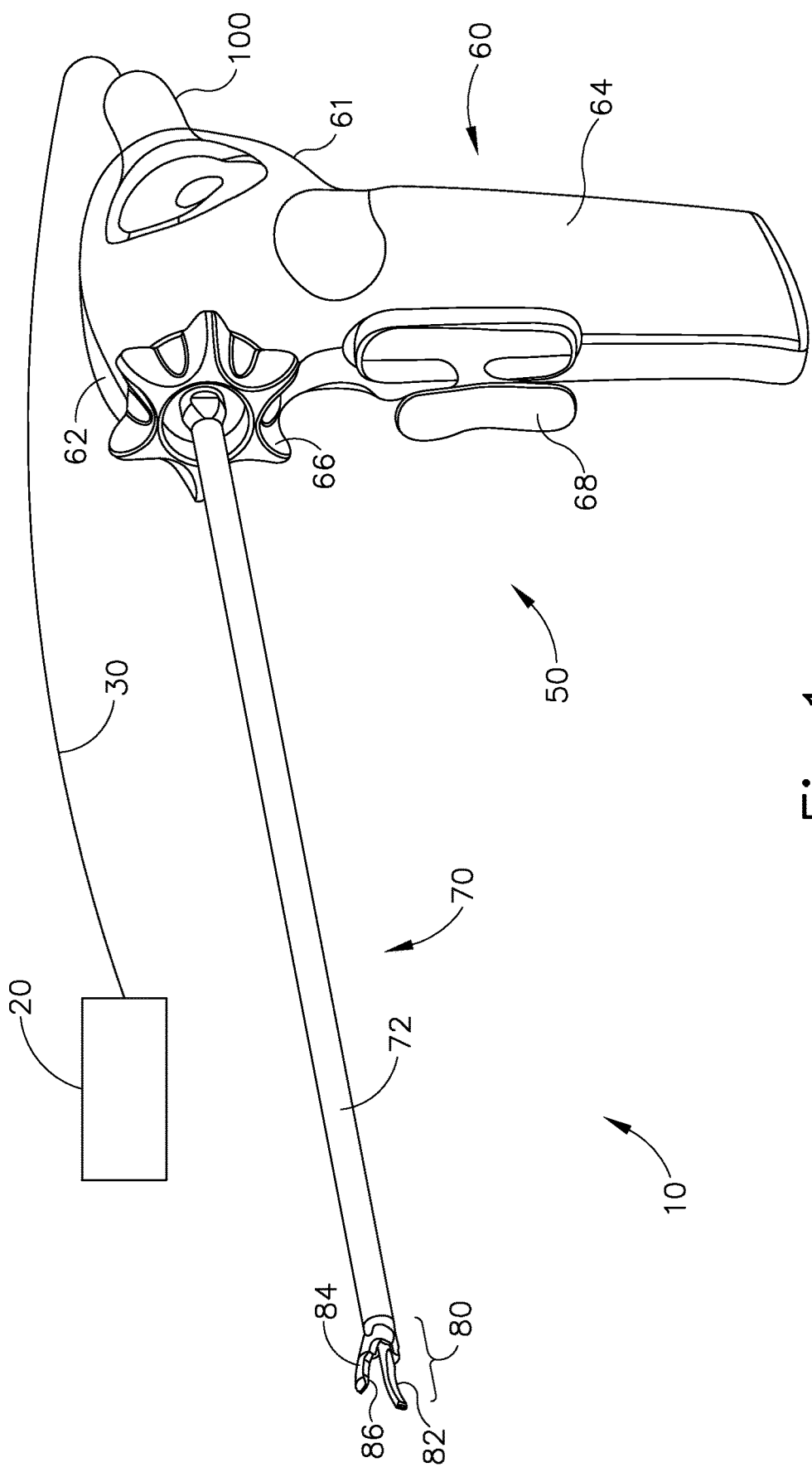
FIG. 1 depicts a perspective view of an exemplary surgical system having a surgical instrument and a generator.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Ultrasonic Surgical System

FIG. 1 shows an exemplary ultrasonic surgical system (10) comprising an ultrasonic surgical instrument (50), a generator (20), and a cable (30) coupling generator (20) to surgical instrument (50). In some versions, generator (20) comprises a GEN 300 sold by Ethicon Endo-Surgery, Inc. of Cincinnati, Ohio. By way of example only, generator (20) may be constructed in accordance with the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. While surgical instrument (50) is described herein as an ultrasonic surgical instrument, it should be understood that the teachings herein may be readily applied to a variety of surgical instruments, including but not limited to endocutters, graspers, cutters, staplers, clip appliers, access devices, drug/gene therapy delivery devices, and energy delivery devices using ultrasound, RF, laser, etc., and/or any combination thereof as will be apparent to one of ordinary skill in the art in view of the teachings herein. Moreover, while the present example will be described in reference to a cable-connected surgical instrument (50), it should be understood that surgical instrument (50) may be adapted for cordless operation, such as that disclosed in U.S. Pat. Pub. No. 2009/0143797, entitled "Cordless Hand-held Ultrasonic Cautery Cutting Device," published Jun. 4, 2009, issued as U.S. Pat. No. 8,419,757 on Apr. 16, 2013, the disclosure of which is incorporated by reference herein. For instance, surgical device (50) may include an integral and portable power source such as a battery, etc. Furthermore, surgical device (50) may also be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

Surgical instrument (50) of the present example includes a multi-piece handle assembly (60), an elongated transmission assembly (70), and a transducer (100). Transmission assembly (70) is coupled to multi-piece handle assembly (60) at a proximal end of transmission assembly (70) and extends distally from multi-piece handle assembly (60). In the present example, transmission assembly (70) is configured as an elongated, thin tubular assembly for endoscopic use, but it should be understood that transmission assembly (70) may alternatively be a short assembly, such as those disclosed in U.S. Pat. Pub. No. 2007/0282333, entitled "Ultrasonic Waveguide and Blade," published Dec. 6, 2007, now abandoned, and U.S. Pat. Pub. No. 2008/0200940, entitled "Ultrasonic Device for Cutting and Coagulating," published Aug. 21, 2008, now abandoned, the disclosures of which are incorporated by reference herein. Transmission assembly (70) of the present example comprises an outer sheath (72), an inner tubular actuating member (not shown), a waveguide (not shown), and an end effector (80) located on the distal end of transmission assembly (70). In the present example, end effector (80) comprises a blade (82) that is mechanically and acoustically coupled to the waveguide, a clamp arm (84) operable to pivot at the proximal end of transmission assembly (70), and a clamp pad (86) coupled to clamp arm (84). In some versions, transducer (100) comprises a plurality of piezoelectric elements (not shown) that are compressed between a first resonator (not shown) and a second resonator (not shown) to form a stack of piezoelectric elements. The piezoelectric elements may be fabricated from any suitable material, for example, lead zirconate-titanate, lead meta-niobate, lead titanate, and/or any suitable piezoelectric crystal material, for example.

Transducer (100) further comprises electrodes, including at least one positive electrode and at least one negative electrode, that are configured to create a voltage potential across the one or more piezoelectric elements, such that the piezoelectric elements convert the electrical power into ultrasonic vibrations. When transducer (100) of the present example is activated, transducer (100) is operable to create linear oscillations or vibrations (e.g., torsional or transverse, etc.) at an ultrasonic frequency (such as 55.5 kHz). When transducer (100) is coupled to transmission assembly (70), these linear oscillations are transmitted through the internal waveguide of transmission assembly (70) to end effector (80). In the present example, with blade (82) being coupled to the waveguide, blade (82) thereby oscillates at the ultrasonic frequency. Thus, when tissue is secured between blade (82) and clamp arm (84), the ultrasonic oscillation of blade (82) may simultaneously sever the tissue and denature the proteins in adjacent tissue cells, thereby providing a coagulative effect with relatively little thermal spread. An electrical current may also be provided through blade (82) and clamp arm (84) to cauterize the tissue. One merely exemplary suitable ultrasonic transducer (100) is Model No. HP054, sold by Ethicon Endo-Surgery, Inc. of Cincinnati, Ohio, though it should be understood that any other suitable transducer may be used. It should also be understood that clamp arm (84) and associated features may be constructed and operable in accordance with at least some of the teachings of U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein.

Multi-piece handle assembly (60) of the present example comprises a mating housing portion (62) and a lower portion (64). Mating housing portion (62) defines a cavity within multi-piece handle assembly (60) and is configured to receive transducer (100) at a proximal end of mating housing portion (62) and to receive the proximal end of transmission assembly (70) at a distal end of mating housing portion (62). A rotation knob (66) is shown in the present example to rotate transmission assembly (70) and transducer (100), but it should be understood that rotation knob (66) is merely optional. Lower portion (64) of multi-piece handle assembly (60) shown in FIG. 1 includes a trigger (68) and is configured to be grasped by a user using a single hand. One merely exemplary alternative version for lower portion (64) is depicted in FIG. 1 of U.S. Pat. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein. Toggle buttons (69), shown in FIG. 2 of the present disclosure, are located on a distal surface of lower portion (64) and are operable to selectively activate transducer (100) at different operational levels using generator (20). For instance, a first toggle button (69) may activate transducer (100) at a maximum energy level while a second toggle button (69) may activate transducer (100) at a minimum, non-zero energy level. Of course, toggle buttons (69) may be configured for energy levels other than a maximum and/or minimum energy level as will be apparent to one of ordinary skill in the art in view of the teachings herein. Furthermore, any other number of toggle buttons may be provided.

While multi-piece handle assembly (60) has been described in reference to two distinct portions (62, 64), it should be understood that multi-piece handle assembly (60) may be a unitary assembly with both portions (62, 64) combined. Multi-piece handle assembly (60) may alternatively be divided into multiple discrete components, such as a separate trigger portion (operable either by a user's hand or foot) and a separate mating housing portion (62). Such a trigger portion may be operable to activate transducer (100) and may be remote from mating housing portion (62). Multi-piece handle assembly (60) may be constructed from a durable plastic casing (61) (such as polycarbonate or a liquid crystal polymer), ceramics, metals and/or any other suitable material as will be apparent to one of ordinary skill in the art in view of the teachings herein. Other configurations for multi-piece handle assembly (60) will also be apparent to those of ordinary skill in the art in view of the teachings herein. For instance, in some versions trigger (68) may be omitted and surgical instrument (50) may be activated by a controlled of a robotic system. In other versions, surgical instrument (50) may be activated when coupled to generator (20).

Further still, surgical instrument (50) may be constructed in accordance with at least some of the teachings of U.S. Pat. No. 5,322,055 entitled "Clamp Coagulator/Cutting System for Ultrasonic Surgical Instruments," issued Jun. 21, 1994, the disclosure of which is incorporated by reference herein; U.S. Pat. No. 5,873,873 entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811 entitled "Blades with Functional Balance Asymmetries for use with Ultrasonic Surgical Instruments," issued Dec. 4, 2001, the disclosure of which is incorporated by reference herein; U.S. Pub. No. 2006/0079874 entitled "Tissue Pad for Use with an Ultrasonic Surgical Instrument," published Apr. 13, 2006, now abandoned, the disclosure of which is incorporated by reference herein; U.S. Pub. No. 2007/0191713 entitled "Ultrasonic Device for Cutting and Coagulating," published Aug. 16, 2007, now abandoned, the disclosure of which is incorporated by reference herein; U.S. Pub. No. 2007/0282333 entitled "Ultrasonic Waveguide and Blade," published Dec. 6, 2007, now abandoned, the disclosure of which is incorporated by reference herein; U.S. Pub. No. 2008/0200940 entitled "Ultrasonic Device for Cutting and Coagulating," published Aug. 21, 2008, now abandoned, the disclosure of which is incorporated by reference herein; U.S. Pub. No. 2009/0143797, entitled "Cordless Hand-held Ultrasonic Cautery Cutting Device," published June 4, 2009, issued as U.S. Pat. No. 8,419,757 on Apr. 16, 2013, the disclosure of which is incorporated by reference herein; U.S. Pub. No. 2010/0069940 entitled "Ultrasonic Device for Fingertip Control," published Mar. 18, 2010, issued as U.S. Pat. No. 9,023,071 on May 5, 2015, the disclosure of which is incorporated by reference herein; U.S. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; and/or U.S. Provisional Application Ser. No. 61/410,603, filed Nov. 5, 2010, entitled "Energy-Based Surgical Instruments," the disclosure of which is incorporated by reference herein.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

II. Exemplary Coupling Mechanisms for Ultrasonic Surgical Instrument

In some instances it may be useful to selectively couple transducer (100) to transmission assembly (70) without using a torque wrench to tighten transducer (100) onto transmission assembly (70). For instance, various mechanical couplings may be implemented that, when cammed or actuated into a locked position, ensure an adequate acoustic coupling of transducer (100) to transmission assembly (70) to permit energy transmission from transducer (100) to blade (82) of end effector (80). Such mechanical couplings may also permit a user to quickly connect and/or disconnect transducer (100) and/or transmission assembly (70) from each other and/or from multi-piece handle assembly (60). In addition, a user may only need to ensure that the coupling mechanism is in the locked position to ensure a sufficient connection, instead using a torque wrench to determine the proper torque. Furthermore, such coupling mechanisms may permit multi-piece handle assembly (60), transmission assembly (70) and/or transducer (100) to be reusable and/or interchangeable. Accordingly, surgical instruments (50) incorporating such coupling mechanisms may be preferable to some users.

A. Exemplary Pin and Troughed Gear Coupling Mechanism

Figure 2:
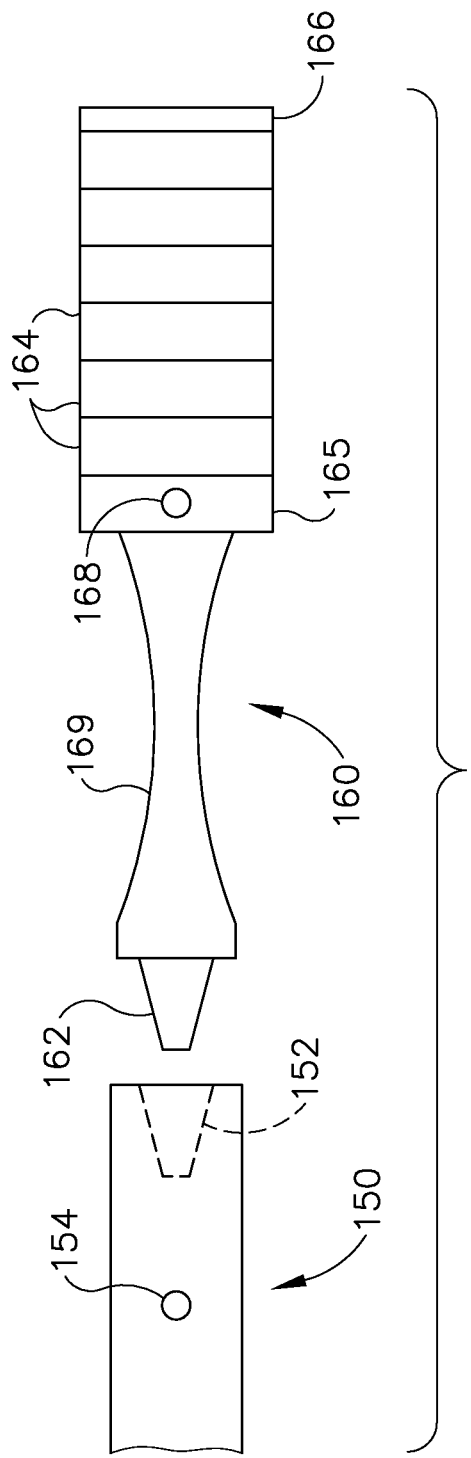
FIG. 2 depicts partial side view of an exemplary transmission assembly and an exemplary transducer having a conical coupling.

FIGS. 2-4B show an exemplary pin and troughed gear coupling mechanism configured to couple a waveguide (150) to a transducer (160). FIG. 2 depicts an exemplary waveguide (150) and an exemplary transducer (160) configured to couple together via a cone (162) and a conical recess (152) (shown in phantom). Waveguide (150) of the present example comprises a conical recess (152) formed in the proximal end and a pin hole (154) through which a first pin (194), shown in FIGS. 4A-4B, may be inserted. Pin hole (154) is located on waveguide (150) at a location corresponding to a node of waveguide (150). A node is a point where the displacement due to the ultrasonic vibrations transmitted through waveguide (150) is at zero. In the present example, waveguide (150) comprises a titanium rod extending though a transmission assembly, such as transmission assembly (70), and terminating with an end effector, such as end effector (80), at a distal end. In some versions, the end effector includes a blade and a clamp arm to simultaneously sever the tissue and denature the proteins in adjacent tissue cells, thereby providing a coagulative effect with relatively little thermal spread. In other versions, the end effector may only include a blade. Still other configurations for the end effector will be apparent to one of ordinary skill in the art in view of the teachings herein.

Transducer (160) of the present example comprises a plurality of piezoelectric elements (164) that are compressed between a first resonator (165) and a second resonator (166) to form a stack of piezoelectric elements. First resonator (165) of the present example further comprises a pin hole (168) through which a second pin (196), shown in FIGS. 4A-4B, may be inserted. Pin hole (168) is located on first resonator (165) at a location corresponding to a node of transducer (160). A node is a point where the displacement due to the ultrasonic vibrations transmitted through transducer (160) is at zero. The piezoelectric elements (164) may be fabricated from any suitable material, for example, lead zirconate-titanate, lead meta-niobate, lead titanate, and/or any suitable piezoelectric crystal material. Transducer (160) further comprises electrodes (not shown), including at least one positive electrode and at least one negative electrode, that are configured to create a voltage potential across the plurality of piezoelectric elements (164), such that the plurality of piezoelectric elements (164) convert the electrical power into ultrasonic vibrations. A distal horn (169) terminates with a cone (162) at the distal end. Cone (162) is sized and configured to insert into conical recess (152) of waveguide (150) to couple transducer (160) to waveguide (150). Other versions may include a hemisphere and hemispherical recess for transducer (160) and waveguide (150), respectively. Of course, cone (162) and conical recess (152) may be omitted and transducer (160) may simply abut against waveguide (150). In the present example, the interface between cone (162) and conical recess (152) is located at a node, though this is merely optional. Indeed, in some versions the interface may be at an antinode, where the displacement due to the ultrasonic vibrations transmitted through transducer (160) is at a maximum, or at a point between a node and antinode. Still other configurations for coupling waveguide (150) to transducer (160) may include those disclosed in U.S. Pat. No. 6,051,010, entitled "Methods and Devices for Joining Transmission Components," issued Apr. 18, 2000. Still other configurations for transducer (160) and/or waveguide (150) will be apparent to one of ordinary skill in the art in view of the teachings herein. For instance, pin holes (154, 168) may be omitted and the pins may be integrally formed on waveguide (150) and/or first resonator (165). Alternatively, the pins may extend out from an outer sheath covering waveguide (150) and/or transducer (160). In such a version, the pins may be isolated from the acoustic components of waveguide (150) and/or transducer (160).

Figure 3:
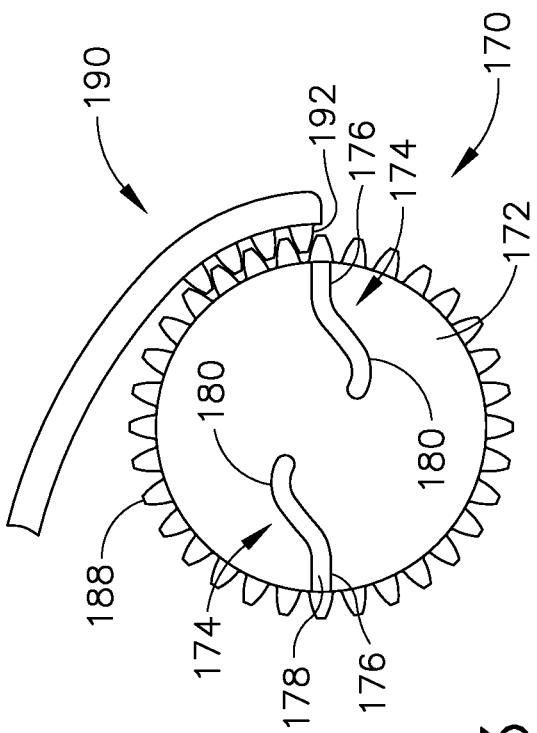
FIG. 3 depicts a side view of an exemplary troughed gear showing a pair of troughs, gear teeth, and a pawl.
Figure 4A:
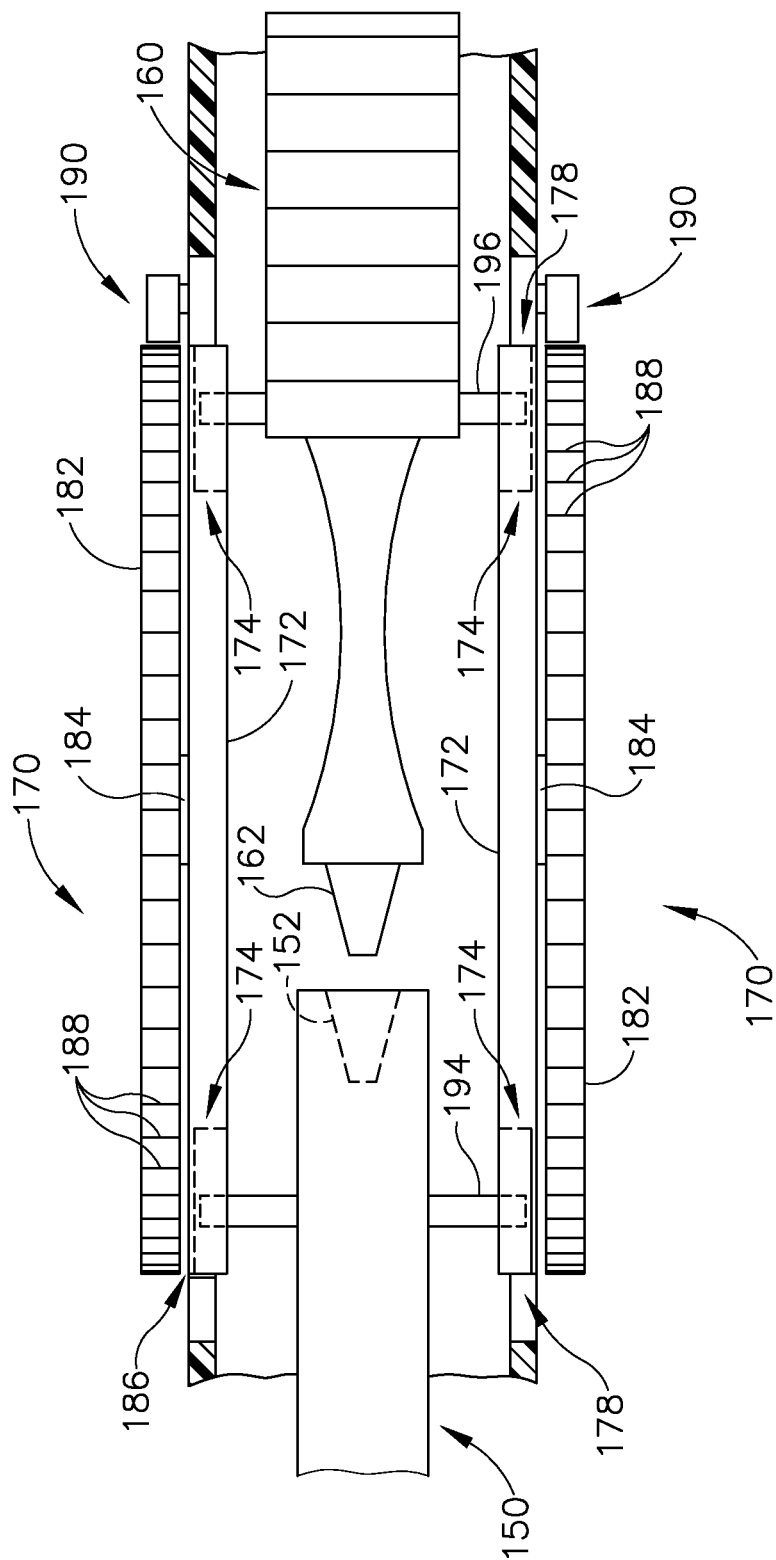
FIG. 4A depicts a top view of an exemplary coupling mechanism utilizing the transmission assembly and transducer of FIG. 2 and the troughed gear of FIG. 3 shown in an unlocked position.

FIG. 3 depicts an exemplary troughed gear (170) and a pawl (190). Troughed gear (170) comprises a first half (172) having a pair of troughs (174) formed therein. In the present example, troughs (174) extend only partially into troughed gear (170), though it should be understood that in other versions troughs (174) may extend entirely through troughed gear (170). Troughs (174) of the present example include an entrance portion (176) and an arcuate portion (180). Entrance portion (176) is a substantially straight channel formed in first half (172) having an open end (178) configured to receive a portion of pin (194, 196), shown in FIGS. 4A-4B. Arcuate portions (180) are curved channels that curve inwardly towards the center of troughed gear (170). Arcuate portions (180) of the present example are designed to guide pin (194, 196) within arcuate portion (180) inwardly along the curvature of arcuate portion (180) as troughed gear (170) is rotated. The movement of pins (194, 196) within arcuate portions (180) will be described in greater detail below. Referring to FIG. 4A, troughed gear (170) further comprises a second half (182) fixedly coupled to first half (172) via an axle (184). A gap (186) between first half (172) and second half (182) permits troughed gear (170) to be coupled to a casing, such as casing (61), with second half (182) located on the outside of the casing and first half (172) located on the inside of the casing. Second half (182) further comprises a plurality of teeth (188) circumferentially disposed about second half (182). Referring back to FIG. 3, pawl (190) is also shown having teeth (192) that complement teeth (188) such that pawl (190) engages and restricts the rotation of troughed gear (170). In the example shown in FIGS. 4A-4B, pawl (190) is a rotatable member coupled to the casing that includes a lever portion (not shown) and a return spring (not shown) to selectively disengage pawl (190) from troughed gear (170). The return spring biases pawl (190) into engagement with teeth (188). In some versions a slidable or translatable member having teeth may engage teeth (188) to prevent rotation of troughed gear (170). Still other configurations for troughed gear (170) and/or pawl (190) will be apparent to one of ordinary skill in the art in view of the teachings herein.

FIG. 4A depicts waveguide (150) and transducer (160) with pins (194, 196) inserted through pin holes (154, 168), shown in FIG. 2, and extending into troughs (174) (shown in phantom) of a pair of opposing troughed gears (170). In the present example, first halves (172) of troughed gears (170) are located within the casing and second halves (182) are located on the exterior of the casing. Axles (184) extend through openings in the casing to couple first and second halves (172, 182) together. Pawls (190) are also located on the exterior of the casing and are configured to selectively engage teeth (188) of troughed gears (170). As shown, pins (194, 196) extend through transducer (160) and waveguide (150) and are inserted through open ends (178) of troughs (174). It should be understood that open ends (178) of troughs (174) permit both waveguide (150) and transducer (160) to be decoupled from troughed gear (170). For instance, waveguide (150) may be a disposable component and transducer (160) may be a reusable component such that decoupling waveguide (150) permits a user to dispose of waveguide (150) and decoupling transducer (160) permits a user to reuse transducer (160) with other surgical instruments. Such removable components may also allow a user to reuse the handle assembly for other procedures as well. Of course, waveguide (150) and/or transducer (160) may instead be non-removable and troughs (174) may instead have closed ends to retain pins (194, 196) therein. In the example shown in FIG. 4A, transducer (160) and waveguide (150) are shown decoupled and in an unlocked position.

When a user desires to couple transducer (160) to waveguide (150), the user rotates troughed gears (170). A lever (not shown) or finger grips may be included on troughed gear (170) to aid the user's rotation of troughed gear (170).

Alternatively, a user may simply grasp and rotate second half (182) to rotate troughed gears (170). As the user rotates troughed gears (170), pins (194, 196) engage arcuate portions (180) of troughs (174) and are cammed radially inward by arcuate portions (180). As pins (194, 196) are cammed radially inward, transducer (160) translates distally and waveguide (150) simultaneously translates proximally. The user continues to rotate troughed gears (170) to engage cone (162) with conical recess (152) (shown in phantom). In the present example, arcuate portions (180) terminate at a predetermined point calculated to provide a sufficient compression between transducer (160) and waveguide (150) to ensure that cone (162) adequately couples with conical recess (152) to transmit the ultrasonic vibrations produced by the stacks of piezoelectric elements (164) to waveguide (150). In other versions, arcuate portions (180) may continue to spiral inwardly on troughed gears (170) to permit a user to tighten transducer (160) to waveguide (150) as desired.

Figure 4B:
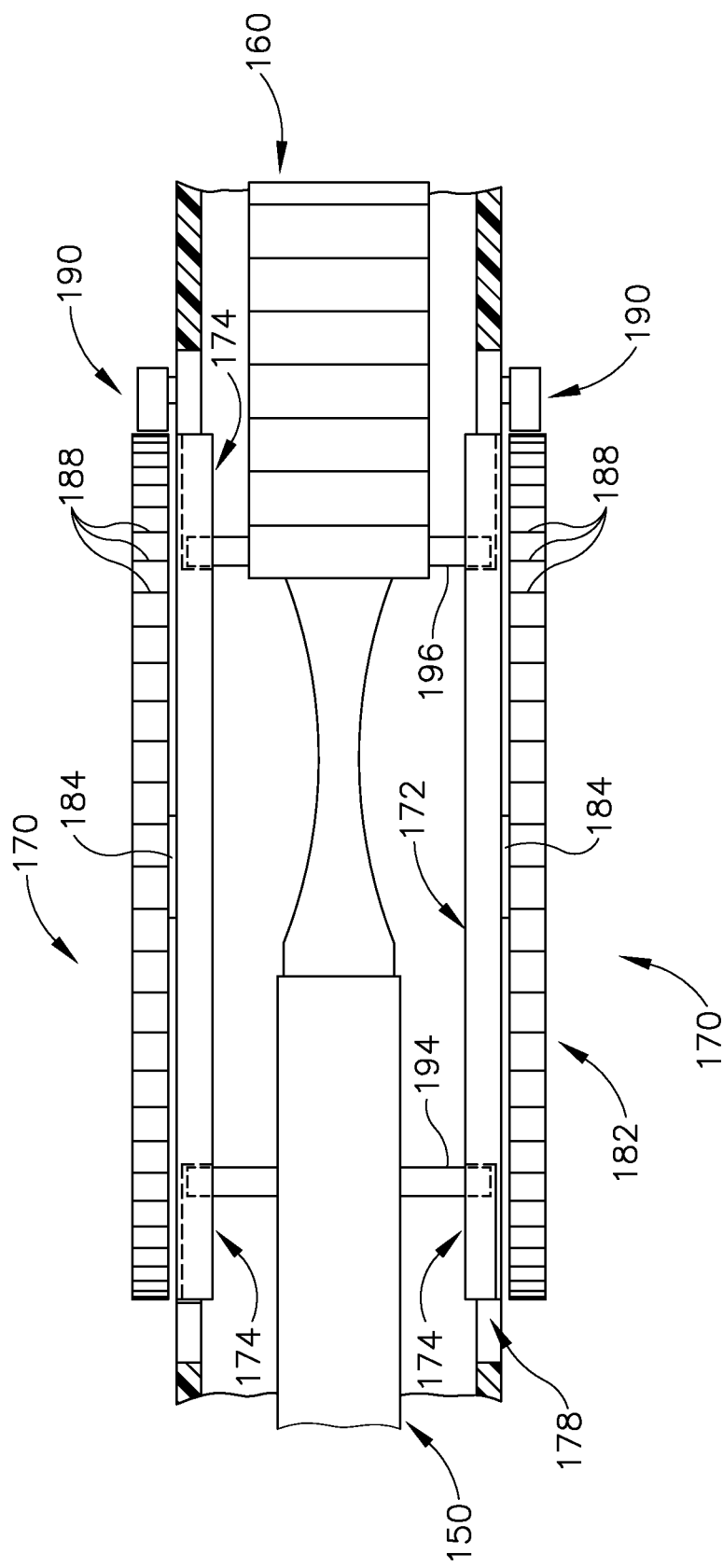
FIG. 4B depicts a top view of the coupling mechanism of FIG. 4A shown in a locked position.

FIG. 4B shows a locked position for the present coupling mechanism showing transducer (160) engaged and coupled to waveguide (150). In the present example, pawls (190) are selectively engaged with teeth (188) of troughed gears (170) to prevent troughed gears (170) from rotating. Accordingly, troughed gears (170), pawls (190), and pins (194, 196) of the present example provide a coupling mechanism for coupling transducer (160) to waveguide (150).

When a user desires to detach transducer (160) and/or waveguide (150), the user disengages pawls (190) from teeth (188) of troughed gears (170). The user may then pull out transducer (160) and/or waveguide (150) (effectively rotating troughed gears (170) via pins (194, 196) and arcuate portions (180)) or rotate troughed gears (170) until pins (194, 196) can be removed through open ends (178) of troughs (174). In some versions, troughed gears (170) may include a torsion spring (not shown) that is biased to rotate troughed gears (170) toward the unlocked position once pawl (190) is disengaged. Thus, a user may quickly connect transducer (160) to waveguide (150) and also ensure an adequate connection between transducer (160) and waveguide (150) by using the pin and troughed gear coupling mechanism described herein.

Of course other configurations for a pin and troughed gear coupling mechanism will be apparent to one of ordinary skill in the art in view of the teachings herein. For instance, a single troughed gear (170) may be used instead of a pair of troughed gears (170). Alternatively, troughed gears (170) may be mechanically coupled together, either directly through an axle or indirectly through additional gears, to concurrently rotate both troughed gears (170). Further still, troughed gears (170) may be located entirely within casing (61) and a key hole (not shown) may be provided to permit a user to insert a geared key to rotate one or both troughed gears (170). Such a key hole and gearing may be configured in similar fashion to the keys used for winding clocks. Further still, troughed gears (170), transducer (160), and waveguide (150) may be contained within a separate casing that is rotatable relative to a main handle assembly. Such a casing may be mounted to the main handle assembly via bearings to permit the rotation of waveguide (150), transducer (160), troughed gears (170), and/or any other components relative to the main handle assembly. Still further configurations will be apparent to one of ordinary skill in the art in view of the teachings herein.

B. Exemplary Sled Coupling Mechanism

Figure 5:
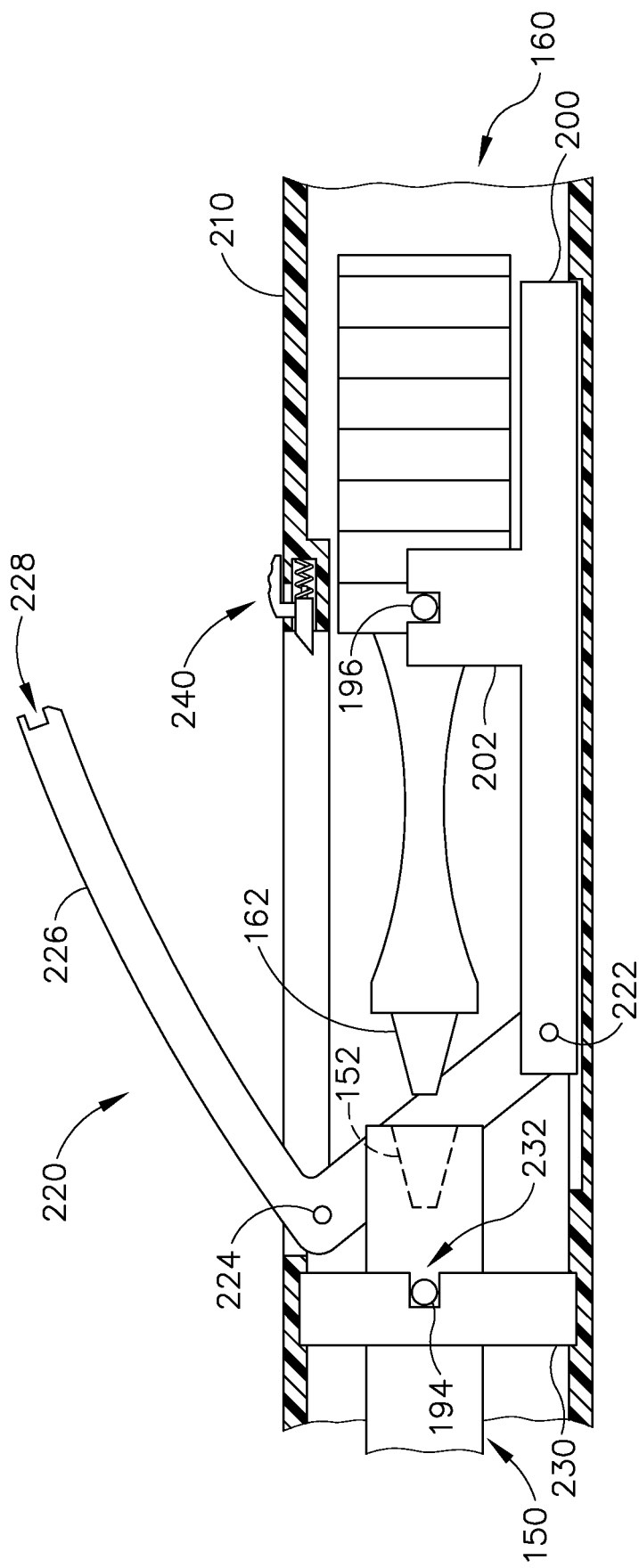
FIG. 5 depicts a side view of an exemplary alternative coupling mechanism having an actuatable sled.

FIG. 5 shows an exemplary sled coupling mechanism for a handle assembly having a casing (210) and configured to couple waveguide (150) to transducer (160) shown and described previously in reference to FIG. 2. In the present example, a sled member (200) includes a pair of U-shaped members (202) configured to receive the ends of pin (196) that extend outwardly from transducer (160). It should be understood that, while a single U-shaped member (202) is shown, a second U-shaped member (202) is located on the opposite side of transducer (160) and is identical to U-shaped member (202) shown. In some versions, U-shaped members (202) may include a resilient snap fastener (not shown) configured to receive and snap the ends of pin (196) into U-shaped members (202), thereby further securing transducer (160) to sled member (200). In addition or in the alternative, U-shaped members (202) may include and/or be coupled to sled member (200) by a resiliently biased member (such as a spring) and/or a force limiting member (not shown). Accordingly, when sled member (200) slidably engages transducer (160) with waveguide (150), the resiliently biased member and/or force limiting member may ensure that the engagement forces between transducer (160) and waveguide (150) are not too high. Of course such resiliently biased member and/or force limiting member may be located anywhere else, including, but not limited to, on waveguide (150) on transducer (160), on pillar (230) (described below), and/or elsewhere.

An actuation arm (220) is coupled to a distal end of sled member (200) by a first axle (222). A second axle (224) couples actuation arm (220) to casing (210) to provide a pivot point about which actuation arm (220) rotates. Actuation arm (220) further includes a handle portion (226) that a user uses to rotate actuation arm (220), as will be described in more detail below. Handle portion (226) includes a recess (228) into which a latch (240) is selectively insertable. Latch (240) includes a spring-loaded camming member and a slidable release to selectively decouple the spring-loaded camming member from handle portion (226). A pair of pillars (230) are located distally of sled member (200) and include a notch (232). It should also be understood that while a single pillar (230) is shown, a pillar (230) is located on the opposite side of waveguide (150) and is identical to pillar (230) shown. Pillars (230) are fixedly attached to casing (210) and notches (232) are configured to receive the ends of pin (194). Notches (232) may also include a resilient snap fastener configured to receive and snap the ends of pin (194) into notch (232). It should be understood that in some versions, waveguide (150) and pin (194) may be affixed to pillar (230) such that waveguide (150) is not removable. Still other configurations for sled member (200) and pillar (230) will be apparent to one of ordinary skill in the art in view of the teachings herein.

Initially, a user couples waveguide (150) to pillars (230) by inserting the ends of pin (194) into notches (232). Pin (196) of transducer (160) is then inserted into U-shaped members (202) of sled member (200). With waveguide (150) prevented from translating distally by notches (232) and transducer (160) longitudinally secured by U-shaped members (202), the user actuates actuation arm (220) by rotating handle portion (226) downwardly toward casing (210). Actuation arm (220) rotates about second axle (224) and translates sled member (200) distally toward waveguide (150) and pillar (230). The user continues to rotate handle portion (226) to engage cone (162) of transducer (160) with conical recess (152) (shown in phantom) of waveguide (150). In present example, sled member (200) and pillar (230) are spaced at a predetermined distance calculated to induce a sufficient compressive force between transducer (160) and waveguide (150) to ensure proper coupling of cone (162) with conical recess (152) when actuation arm (220) is rotated and latch (240) engages recess (228) of handle portion (226). Such a compressive force may be calculated such that the ultrasonic vibrations produced by the stacks of piezoelectric elements (164) are adequately transmitted to waveguide (150). When a user desires to decouple transducer (160) from waveguide (150), latch (240) is released and actuation arm (220) is actuated to translate sled member (200) proximally. The user may then remove transducer (160) and/or waveguide (150) for reuse, disposal, and/or reclamation. Thus, a user may quickly connect transducer (160) to waveguide (150) and also ensure an adequate connection between transducer (160) and waveguide (150) by using the sled coupling mechanism described herein.

Of course other configurations for a sled coupling mechanism will be apparent to one of ordinary skill in the art in view of the teachings herein. For instance, a pair of actuation arms (220) may be located on either side of sled member (200). Alternatively, in versions in which transducer (160) is a cordless transducer, transducer (160) may be affixed to U-shaped members (202) or directly to sled member (200). Further still, a separate casing containing the sled coupling mechanism may be rotatably coupled via bearings to a handle assembly to permit rotation of the entire coupling mechanism relative to the handle assembly. In yet a further configuration, a spring may be provided to resiliently bias sled member (200) proximally such that the user merely needs to release latch (240). Still further configurations will be apparent to one of ordinary skill in the art in view of the teachings herein.

C. Exemplary Self-Locking Pin and Lever Coupling Mechanism

Figure 6A:
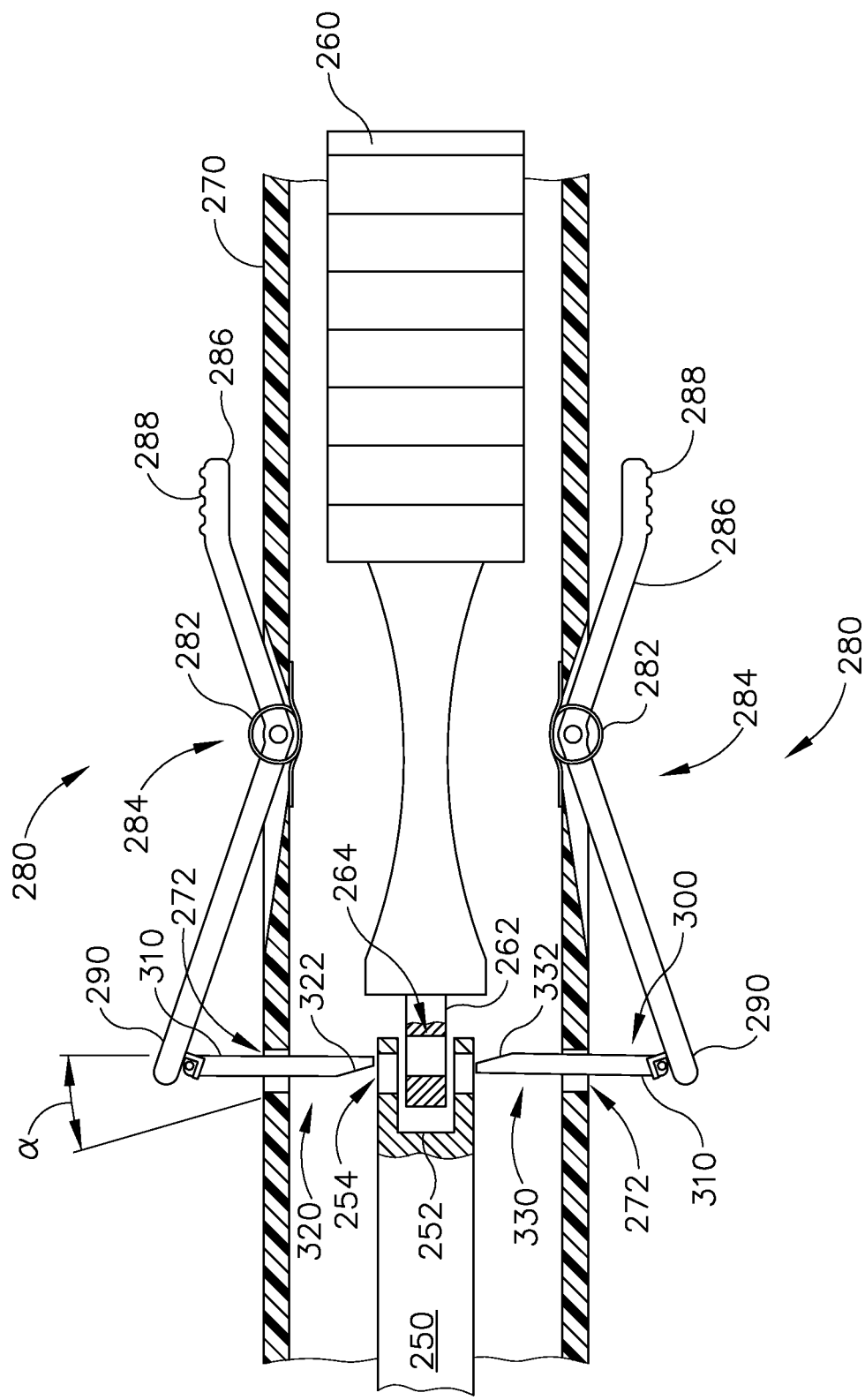
FIG. 6A depicts a partial top cross-sectional view of another exemplary coupling mechanism having a self-locking pin assembly and shown in an unlocked position.
Figure 6B:
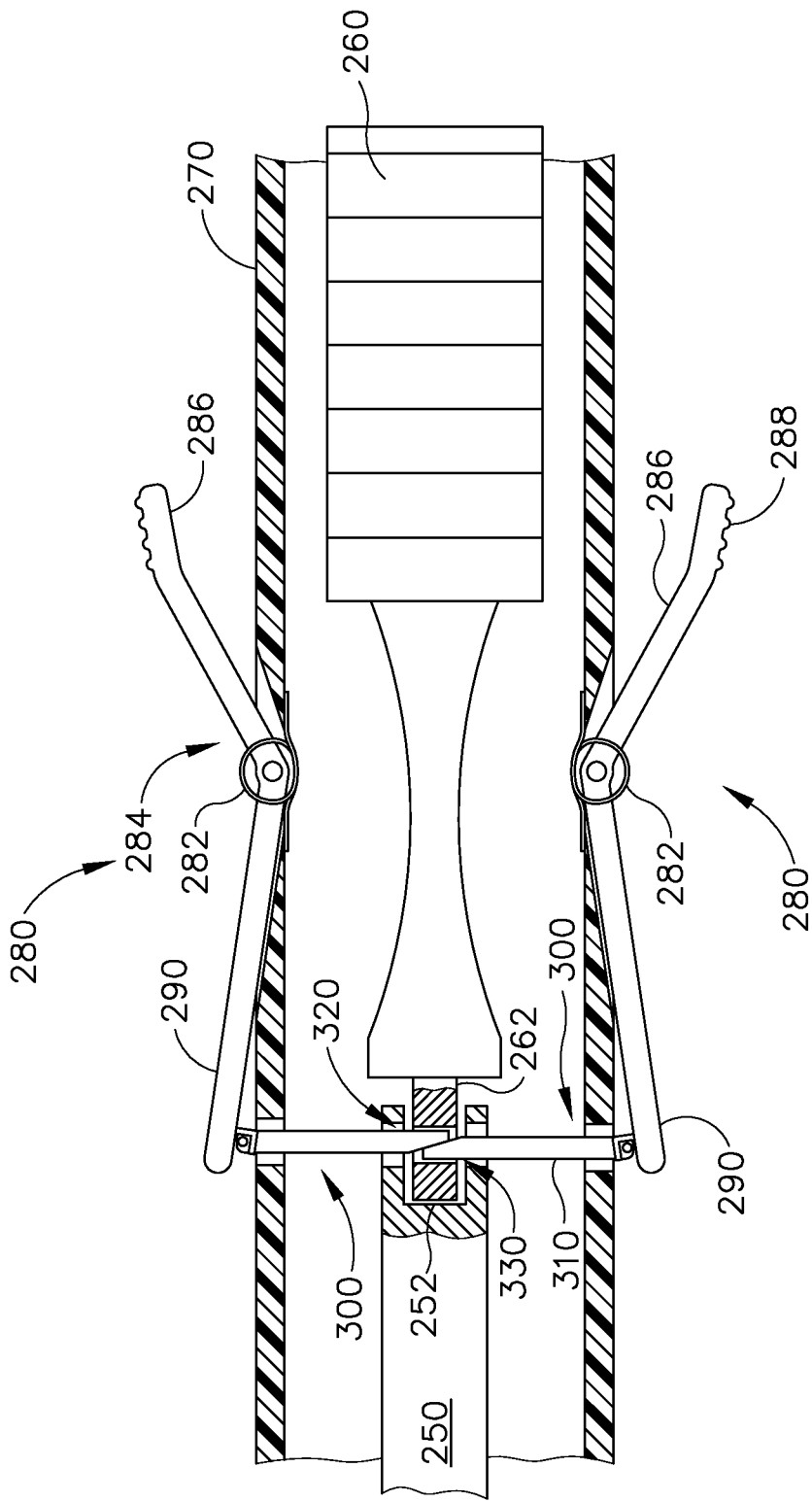
FIG. 6B depicts a partial top cross-sectional view of the coupling mechanism of FIG. 6A shown in a locked position.
Figure 7:
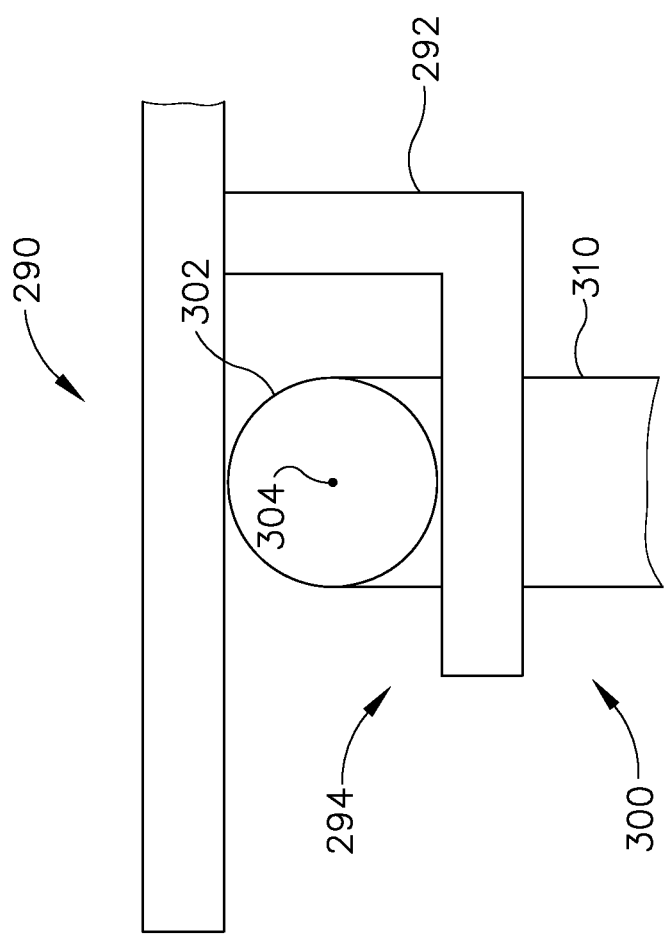
FIG. 7 depicts an enlarged top view of a wheel of the locking pin assembly of FIG. 6A.

FIGS. 6A-7 show yet another coupling mechanism that includes a self-locking pin and lever coupling mechanism. As shown in FIGS. 6A-6B, an exemplary waveguide (250) and an exemplary transducer (260) are configured to couple together via a horn (262) and a recess (252). Horn (262) includes a transaxial pin hole (264) configured to receive first and second pin ends (320, 330), described in more detail below. Transaxial pin hole (264) of the present example is located at a node of transducer (260), though this is merely optional. Waveguide (250) also includes a transaxial pin hole (254) that transects recess (252) and, as shown in FIG. 6B, at least partially aligns with transaxial pin hole (264) of horn (262) when first and second pin ends (320, 330) are inserted therein. Transaxial pin hole (254) of the present example is likewise located at a node of waveguide (250), though this is also merely optional. In the present example, waveguide (250) comprises a titanium rod that terminates at a distal end with an end effector, such as end effector (80). Waveguide (250) may also be included in a transmission assembly, such as transmission assembly (70) described above. In some versions, the end effector includes a blade and a clamp arm to simultaneously sever the tissue and denature the proteins in adjacent tissue cells, thereby providing a coagulative effect with relatively little thermal spread. In other versions, the end effector may only include a blade. Still other configurations for the end effector will be apparent to one of ordinary skill in the art in view of the teachings herein.

An outer casing (270) of a handle assembly, such as multi-piece handle assembly (60), includes a pair of pin apertures (272) and a pair of pin and lever assemblies (280). In the present example, pin and lever assemblies (280) are located on opposing sides of casing (270), though in some versions a pin and lever assembly (280) may be located on the top of casing (270) and a second pin and lever assembly (280) may be located on the bottom of casing (270). Further still, pin and lever assemblies (280) do not need to be directly opposed. Indeed, in some versions pin and lever assemblies (280) may be disposed in a V shaped arrangement or at any other suitable arrangement as will be apparent to one of ordinary skill in the art in view of the teachings herein. Pin and lever assemblies (280) of the present example are each coupled to casing (270) by a respective axle (not shown) such that pin and lever assemblies (280) are pivotable relative to casing (270). Torsion springs (282) are coupled to pin and lever assemblies (280) and to casing (270) to bias pin and lever assemblies (280) toward a locked position, as shown in FIG. 6B. Pin and lever assemblies (280) each comprise a lever (284) and a pin portion (300). Lever (284) includes a handle (286) extending proximally away from the axle and torsion spring (282) and a lever portion (290) extending distally from the axle torsion spring (282). Handle (286) includes thumb treads (288) to provide a ridged surface for a user to press upon, though this is merely optional.

Referring now to FIG. 7, lever portion (290) further comprises an L-shaped member (292) defining a ledge (294). Pin portion (300) includes a wheel (302) that is rotatably coupled to a pin body (310) and insertable onto ledge (294). Wheel (302) of the present example comprises a rotatable Teflon® (of E. I. du Pont de Nemours and Company of Wilmington, Del.) wheel coupled to an axle (304) and rotatable relative to pin body (310). When wheel (302) is placed upon ledge (294), ledge (294) permits wheel (302) to slide and/or roll on ledge (294) while substantially restricting the vertical movement of wheel (302). Thus, if ultrasonic vibrations are transmitted to pin portions (300), then wheels (302) slide and/or roll on ledges (294) to reduce the transmission of the ultrasonic vibrations to levers (284). In one alternative, a Teflon® cap may be used instead of wheel (302) such that Teflon® cap only slides on ledge (294). Of course other materials may be used, including rubber, plastic, and/or any other acoustically isolating material as will be apparent to one of ordinary skill in the art in view of the teachings herein.

Referring back to FIGS. 6A-6B, the ends of pin bodies (310) opposite of wheels (302) terminate at a first pin end (320) or second pin end (330). First pin end (320) comprises a ramped portion (322) having a wedge angle $\alpha$. By way of example only, wedge angle $\alpha$ may be between about 10 degrees, inclusive, and about 20 degrees, inclusive. It should be understood that wedge angle $\alpha$ may be as small as 0.01 degree or as large as 45 degrees. Second pin end (330) also includes a ramped portion (332) with a wedge angle $\alpha$; however, ramped portion (332) of second pin end (330) is oriented in the opposite direction relative to ramped portion (322) of first pin end (320) such that ramped portions (322, 332) are parallel planar portions and the wedge angles are alternate interior angles. As will be appreciated by one of ordinary skill in the art, when ramped portions (322, 332) are not engaged, first pin end (320) and second pin end (330) do not overlap. As shown in FIG. 6B, when ramped portions (322, 332) engage, ramped portions (322, 332) slide against each other and cam first and second pin ends (320, 330) outwardly in the longitudinal direction, thereby effectively expanding the longitudinal width that first and second pin ends (320, 330) occupy. Accordingly, as shown in FIG. 6B, when first and second pin ends (320, 330) engage within transaxial pin hole (264), the camming of ramped portions (322, 332) against each other urges horn (262) of transducer (260) into recess (252) of waveguide (250).

When a user desires to couple transducer (260) to waveguide (250), initially the user rotates handles (286) of both pin and lever assemblies (280) to rotate lever portions (290) about torsion springs (282). The rotation of lever portions (290) engages wheels (302) via L-shaped members (292) to actuate pin portions (300) outwardly relative to pin apertures (272). Tab stops (not shown) may be included on pin bodies (310) to prevent a user from pulling pin portions (300) completely out of pin apertures (272), though this is merely optional. FIG. 6A depicts pin portions (300) outwardly actuated and in an unlocked position. With pin portions in an unlocked position, transducer (260) and/or waveguide (250) are inserted into the handle assembly. Horn (262) is inserted into recess (252) and transaxial pin holes (254, 264) are substantially axially aligned with each other and with first and second pin ends (320, 330), as shown in FIG. 6A. Such alignment may be accomplished using a visual indicator (not shown) on waveguide (250) and/or transducer (260). Alternatively, a key (not shown) and keyway (not shown) may be included on horn (262) and in recess (252), respectively, to physically align transducer (260) with waveguide (250). It should be noted that pin holes (254, 264) need not be completely axially aligned as ramped portions (322, 332) may cam pin holes (254, 256) into complete alignment as ramped portions (322, 332) and first and second pin ends (320, 330) are inserted therethrough.

With transaxial pin holes (254, 264) and first and second pin ends (320, 330) substantially aligned, the user releases handles (286) and torsion springs (282) rotate lever portions (290) inwardly. Lever portions (290) engage wheels (302) to actuate pin portions (300) inwardly relative to pin apertures (272). As pin portions (300) move inwardly, first and second pin ends (320, 330) enter transaxial pin hole (254) of waveguide (250). In the example shown, first pin end (320) and ramped portion (322) may engage transaxial pin hole (264) to cam horn (262) distally as first pin end (320) enters transaxial pin hole (264). If second pin end (330) is misaligned relative to transaxial pin hole (264), the camming of horn (262) distally may align transaxial pin hole (264) to permit second pin end (330) to enter transaxial pin hole (264). First and second pin ends (320, 330) engage each other within transaxial pin hole (264) and ramped portions (322, 332) cam against one another as pin portions (300) continue to actuate inwardly. The engagement of ramped portions (322, 332) within transaxial pin hole (264) urges horn (262) of transducer (260) further into recess (252) of waveguide (250) to couple transducer (260) to waveguide (250). Torsion springs (282) may be designed such that a certain compressive force between horn (262) and a distal wall of recess (252) is achieved when pin and lever assemblies (280) are in the locked position, shown in FIG. 6B. Such a compressive force may be calculated such that the ultrasonic vibrations produced by transducer (260) are adequately transmitted to waveguide (250). In addition or in the alternative, levers (284) may disengage from pin portions (300) once the engagement of transducer (260) with waveguide (250) is made. In such instances, pin portions (300) may be spring biased inwardly. Of course in other versions, waveguide (250) may be translatable proximally in addition to, or in lieu of, horn (262) and transducer (260) translating distally.

When a user desires to decouple transducer (260) from waveguide (250), the user actuates handles (286) to lift pin portions (300) outwardly relative to pin apertures (272). Ramped portions (322, 332) disengage and first and second pin ends (320, 330) are actuated out of transaxial pin holes (254, 264). With first and second pin ends (320, 330) removed, the user may remove waveguide (250) and/or transducer (260) from within casing (270) of the handle assembly. Thus, a user may quickly connect transducer (260) to waveguide (250) and also ensure an adequate connection between transducer (260) and waveguide (250) by using the self-locking pin and lever coupling mechanism described herein.

Of course other configurations for a self-locking pin and lever coupling mechanism will be apparent to one of ordinary skill in the art in view of the teachings herein. For instance, a single pin and lever assembly (280) may be used in which pin body (310) comprises a substantially conical member insertable through conical transaxial pin holes (254, 264) to couple waveguide (250) and transducer (260). In another version, lever (284) may be omitted and pin portions (300) may be spring-biased members each having a handle for a user to outwardly actuate pin portions (300). Still further configurations will be apparent to one of ordinary skill in the art in view of the teachings herein.

D. Exemplary Bolt-Action Coupling Mechanism

Figure 8A:
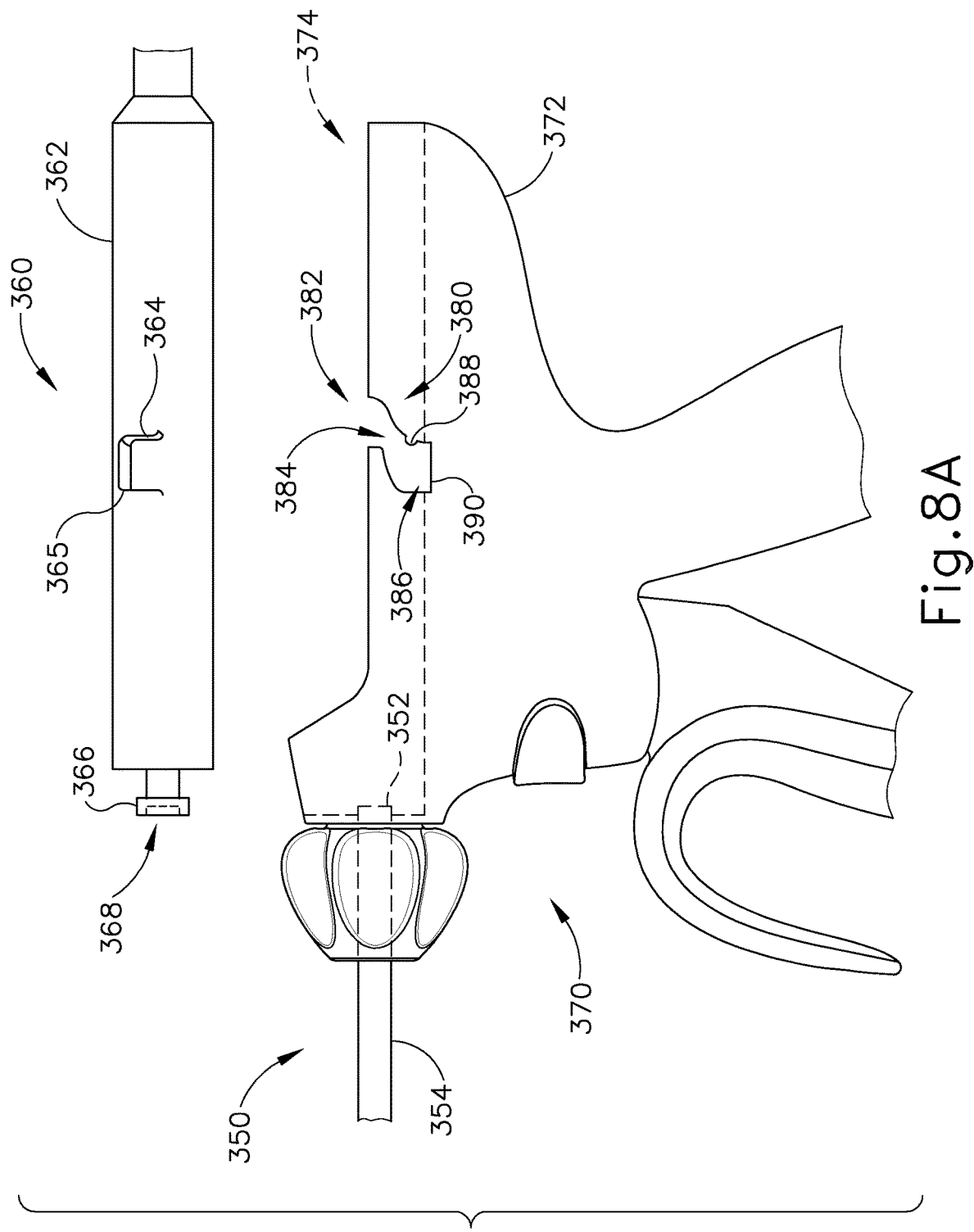
FIG. 8A depicts a side view of another exemplary coupling mechanism for coupling a transducer unit to a waveguide and a handle assembly, showing the transducer unit unlocked.
Figure 8B:
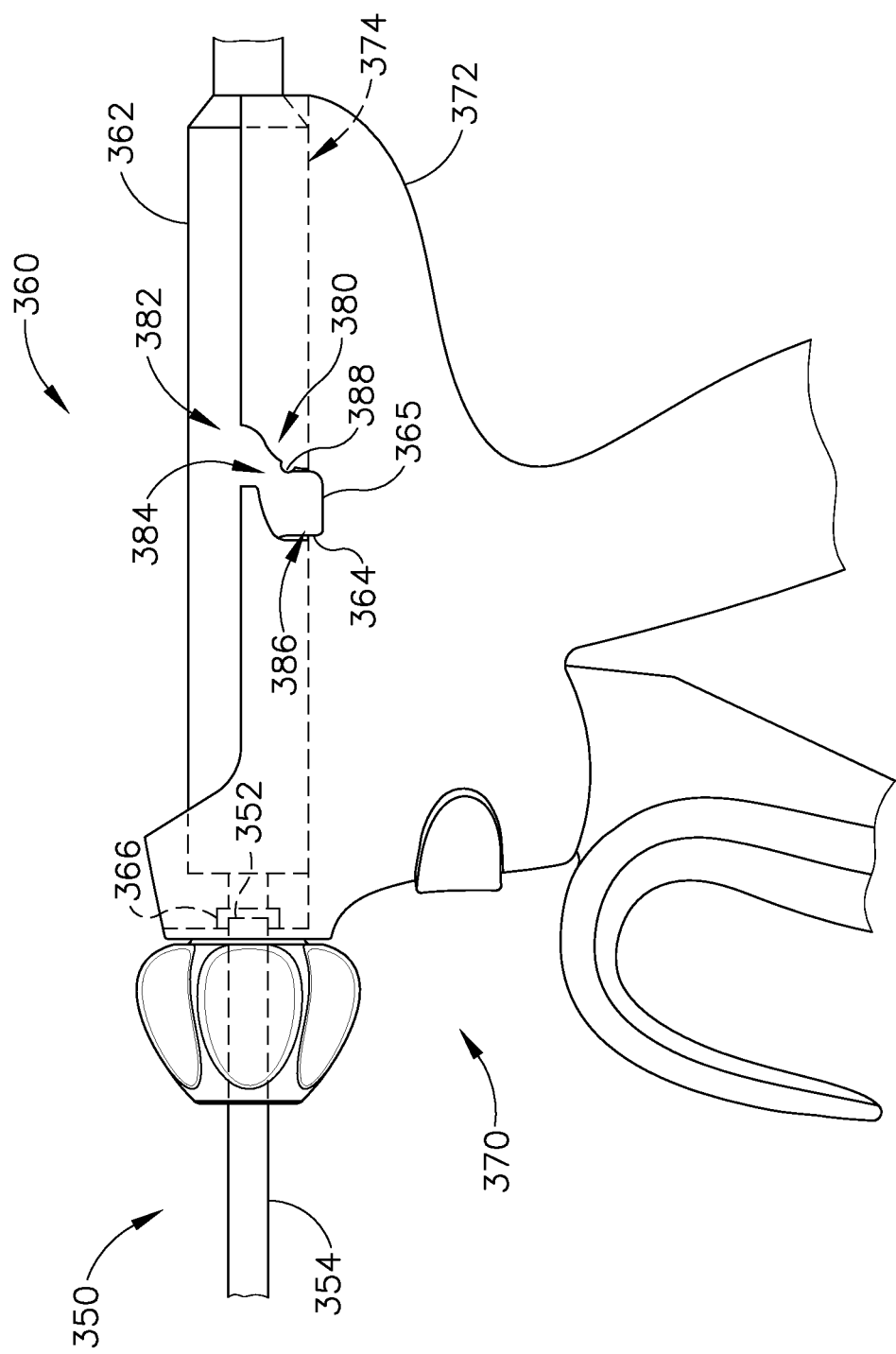
FIG. 8B depicts a side view of the coupling mechanism of FIG. 8A, showing the transducer unit coupled to the waveguide and locked into the handle assembly.

FIGS. 8A-8B depict another coupling mechanism that includes a bolt-action coupling mechanism for coupling a transducer unit (360) to a waveguide (350). Referring initially to FIG. 8A, transducer unit (360) of the present example includes a transducer body (362), a locking member (364), and a distal coupling member (366). Locking member (364) extends radially outward from transducer body (362) at approximately the midpoint along the longitudinal length of transducer body (362). In other versions, locking member (364) may be located near the distal end of transducer body (362) or near the proximal end of transducer body (362). Locking member (364) of the present example further comprises a handle portion (365) with which a user may grasp locking member (364) when locking member (364) is inserted into a ramped cam slot (380), as will be described in greater detail below.

Waveguide (350) of the present example is coupled to a handle assembly (370) with a proximal end (352) (shown in phantom) extending proximally into handle assembly (370) and a distal portion (354) extending distally from handle assembly (370). In the present example, waveguide (350) comprises a titanium rod that terminates at a distal end with an end effector, such as end effector (80). Waveguide (350) may also be included in a transmission assembly, such as transmission assembly (70) described above. In some versions, the end effector includes a blade and a clamp arm to simultaneously sever the tissue and denature the proteins in adjacent tissue cells, thereby providing a coagulative effect with relatively little thermal spread. In other versions, the end effector may only include a blade. Still other configurations for the end effector will be apparent to one of ordinary skill in the art in view of the teachings herein. Proximal end (352) of waveguide (350) is configured to be insertable into a recess (368) (shown in phantom) of distal coupling member (366). In the present example, proximal end (352) is a cylindrical member that is insertable into recess (368) of distal coupling member (366). In other versions, proximal end (352) and distal coupling member (366) may include threading, slots and locking tabs, snap fasteners, and/or any other coupling member as will be apparent to one of ordinary skill in the art in view of the teachings herein.

Handle assembly (370) of the present example includes a casing (372), a portion of which defines a transducer recess (374), and a ramped cam slot (380) formed in casing (372) on a side of transducer recess (374). Handle assembly (370) may further be configured in accordance with at least some of the teachings of multi-piece handle assembly (60) described above; U.S. Pat. Pub. No. 2006/0079874, now abandoned; U.S. Pat. Pub. No. 2007/0191713, now abandoned; U.S. Pat. Pub. No. 2007/0282333, now abandoned; U.S. Pat. Pub. No. 2008/0200940, now abandoned; U.S. Pat. Pub. No. 2011/0015660, issued as U.S. Pat. No. 8,461,744 on Jun. 11, 2013; U.S. Pat. No. 6,500,176; U.S. Pat. Pub. No. 2011/0087218, issued as U.S. Pat. No. 8,939,974 on Jan. 27, 2015; and/or U.S. Pat. Pub. No. 2009/0143797, issued as U.S. Pat. No. 8,419,757 on Apr. 16, 2013. Transducer recess (374) of the present example is sized and configured to receive at least a portion of transducer body (362) when inserted therein. Ramped cam slot (380) comprises dogleg shaped slot having an opening portion (382), a transition portion (384), a locking portion (386), and a detent (388). In the present example, opening portion (382) is configured to receive locking member (364) when transducer unit (360) is initially inserted into transducer recess (374). Transition portion (384) extends distally from opening portion (382) toward proximal end (352) of waveguide (350). Locking portion (386) extends downwardly from transition portion (384) and includes a lower surface (390) and a detent (388) located above lower surface (390). Detent (388) is configured to resist vertical movement of locking member (364) past detent (388) in locking portion (386). As will be apparent to one of ordinary skill in the art, when locking member (386) is urged past detent (388) and toward lower surface (390) of locking portion (386), locking member (364) is secured within locking portion (386) both longitudinally by the sides of locking portion (386) and vertically by detent (388) and lower surface (390). Thus, with locking member (364) secured therein, transducer unit (360) is secured to handle assembly (370). A spring may resiliently bias transducer unit (360) proximally to further ensure locking member (364) is urged past detent (388). The spring may also prevent an inadvertent release of locking member (364) past detent (388).

When a user desires to couple transducer unit (360) to waveguide (350), initially the user inserts transducer unit (360) into transducer recess (374). If locking member (364) is not initially within opening portion (382) of ramped cam slot (380), the user rotates transducer unit (360) until locking member (364) enters opening portion (382). It should be understood at this point that distal coupling member (366) of transducer unit (360) and proximal end (352) of waveguide (350) are substantially axially aligned, but are not coupled together. The user grasps handle portion (365) and actuates locking member (364) distally along transition portion (384). As locking member (364) is actuated distally along transition portion (384), distal coupling member (366) engages and couples to proximal end (352) of waveguide (350). As noted above, proximal end (352) and distal coupling member (366) may alternatively include threading, slots and locking tabs, snap-on fittings, and/or any other coupling member as will be apparent to one of ordinary skill in the art in view of the teachings herein.

Once locking member (364) is at a distal end of transition portion (384), the user rotates locking member (364) into locking portion (386) and past detent (388). The rotation of transducer unit (360) from opening portion (382) until transducer unit (360) is locked in by detent (388) may be between 10 and 350 degrees of rotation. The rotation of transducer unit (360) in the present example is approximately 90 degrees. When locking member (364) is rotated into locking portion (386) of ramped cam slot (380), distal coupling member (366) of transducer unit (360) and proximal end (352) of waveguide (350) are already substantially engaged and distal coupling member (366) of the present example merely rotates about proximal end (352). In other versions, such as in a version including a threaded distal coupling member (366), the threads of distal coupling member (366) may engage and thread into threads of proximal end (352) when locking member (364) is rotated into locking portion (386). By way of example only, a luer lock-type fitting or quarter turn fasteners may be used. In an alternative version having a slot and tab configuration, the rotation of transducer unit (360) may rotate the tab to lock distal coupling member (366) to proximal end (352). Still other configurations for distal coupling member (366) and proximal end (352) will be apparent to one of ordinary skill in the art in view of the teachings herein.

FIG. 8B shows transducer unit (360) coupled to waveguide (350) when locking member (364) is within locking portion (386). A user may then use the assembled surgical instrument for a procedure. To decouple transducer unit (360) from waveguide (350), the user grasps handle portion (365) and urges locking member (364) past detent (388) and out of locking portion (386). The user then actuates locking member (364) proximally along transition portion (384), thereby decoupling transducer unit (360) from waveguide (350). Once locking member (364) is within opening portion (382), the user may lift transducer unit (360) out of transducer recess (374). Handle assembly (370) may then be disposed of, cleaned, and/or reclaimed as desired. Thus, a user may quickly connect transducer unit (360) to waveguide (350) and also ensure an adequate connection between transducer unit (360) and waveguide (350) by using the bolt-action coupling mechanism described herein.

Of course other configurations for a bolt-action coupling mechanism will be apparent to one of ordinary skill in the art in view of the teachings herein. For instance, transducer unit (360) may include bearings to permit rotation of a transducer contained within transducer unit (360) relative to transducer unit (360) and/or handle assembly (370). In another version, transducer recess (374) may be substantially enclosed with an opening at a proximal end of handle assembly (370). In such a version, transition portion (384) or opening portion (382) of ramped cam slot (380) extends proximally such that locking member (364) and transducer unit (360) are longitudinally insertable handle assembly (370). In addition, more than one locking member (364) and more than one ramped cam slot (380) may be used. In yet another alternative, transducer unit (360) may be coupled to handle assembly (370) and locking member (364) may instead be coupled to waveguide (350). In such a version, locking member (364) couples waveguide (350) to transducer unit (360) and handle assembly (370) by rotation and insertion into ramped cam slot (380). Still further configurations will be apparent to one of ordinary skill in the art in view of the teachings herein.

E. Exemplary Camming Lever Arms Coupling Mechanism

Figure 9:
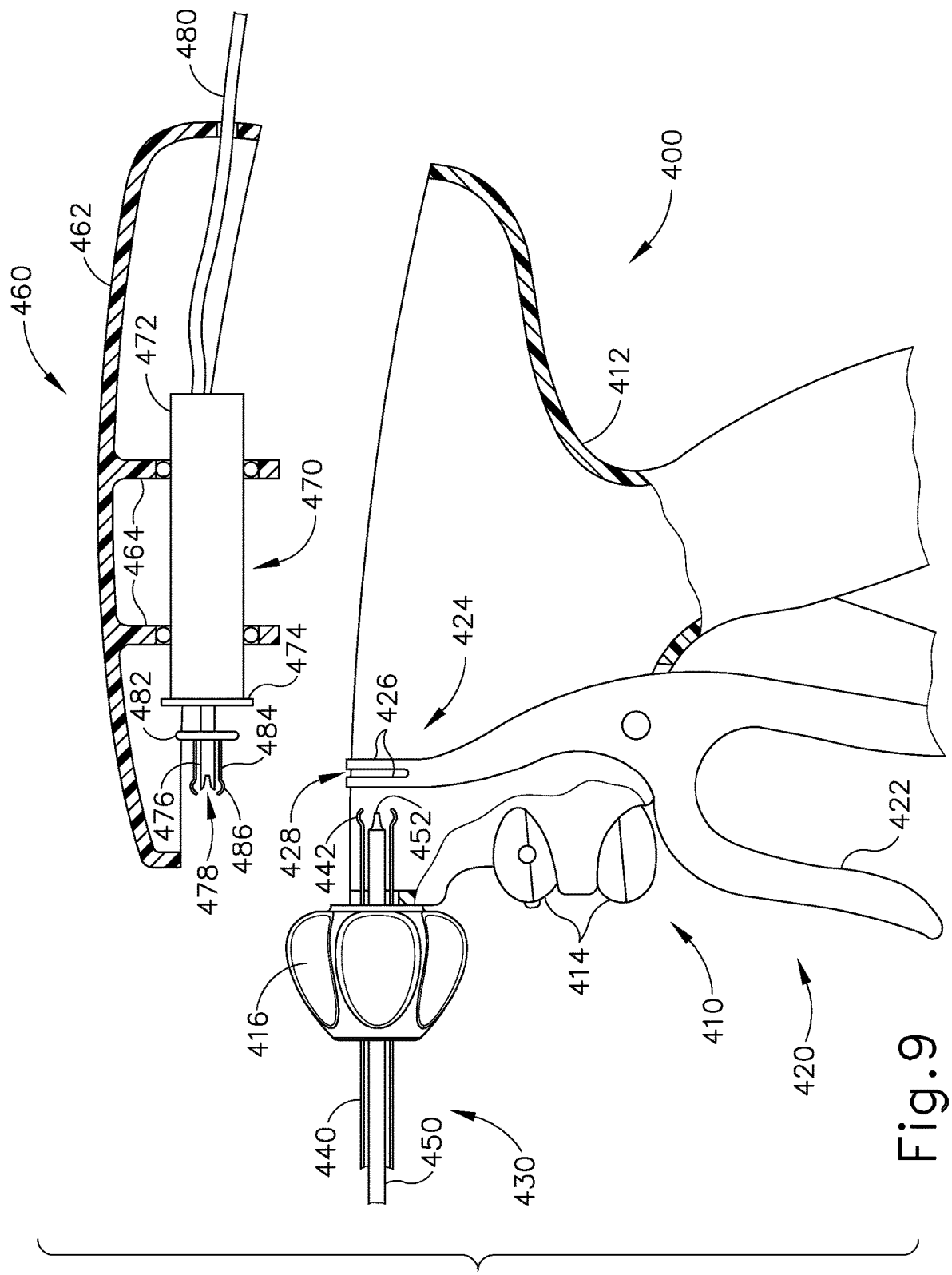
FIG. 9 depicts a side cross-sectional view of yet another coupling mechanism for an exemplary alternative transducer unit and handle assembly, showing the transducer unit in an unlocked position.

FIGS. 9-11B show still another coupling mechanism for an exemplary handle assembly (400) to couple a transducer (470) to a waveguide (450). Referring to FIG. 9, handle assembly (400) of the present example comprises a lower handle portion (410) and a transducer unit (460). Lower handle portion (410) includes a casing (412), a pair of toggle buttons (414), a rotation knob (416), and a trigger (420) pivotably mounted to lower handle portion (410). Casing (412), toggle buttons (414), and/or rotation knob (416) may be configured in accordance with at least some of the teachings of casing (61), toggle buttons (69), and rotation knob (66) described above or in accordance with U.S. Pat.

Pub. No. 2006/0079874, now abandoned; U.S. Pat. Pub. No. 2007/0191713, now abandoned; U.S. Pat. Pub. No. 2007/0282333, now abandoned; U.S. Pat. Pub. No. 2008/0200940, now abandoned; U.S. Pat. Pub. No. 2011/0015660, issued as U.S. Pat. No. 8,461,744 on Jun. 11, 2013; U.S. Pat. No. 6,500,176; U.S. Pat. Pub. No. 2011/0087218, issued as U.S. Pat. No. 8,939,974 on Jan. 27, 2015; and/or U.S. Pat. Pub. No. 2009/0143797, issued as U.S. Pat. No. 8,419,757 on Apr. 16, 2013. A transmission assembly (430) is coupled to rotation knob (416) and a portion of transmission assembly (430) extends distally from lower handle portion (410). In the present example, transmission assembly (430) comprises a waveguide (450) and an outer shaft (440) coaxially disposed about waveguide (450). A proximal end of both waveguide (450) and outer shaft (440) extends proximally of rotation knob (416) and terminates distally of a forked portion (424) of trigger (420), as will be described in more detail below. In the example shown, the proximal end of waveguide (450) comprises a tapered shaft (452) that is configured to couple to a tapered recess (478) of a horn (476) of transducer (470) in transducer unit (460). The proximal end of outer shaft (440) includes a flared snap-on connector (442) configured to snap onto a flared portion (486) of an outer tube (484) of transducer (470). An end effector (not shown) is coupled to the distal end of outer shaft (440) and waveguide (450). The end effector may be configured in accordance with at least some of the teachings of end effector (80) described above. For instance, in one version end effector includes a blade and a clamp arm to simultaneously sever the tissue and denature the proteins in adjacent tissue cells, thereby providing a coagulative effect with relatively little thermal spread. In other versions, end effector may only include a blade. Still other configurations for the end effector will be apparent to one of ordinary skill in the art in view of the teachings herein.

Figure 10:
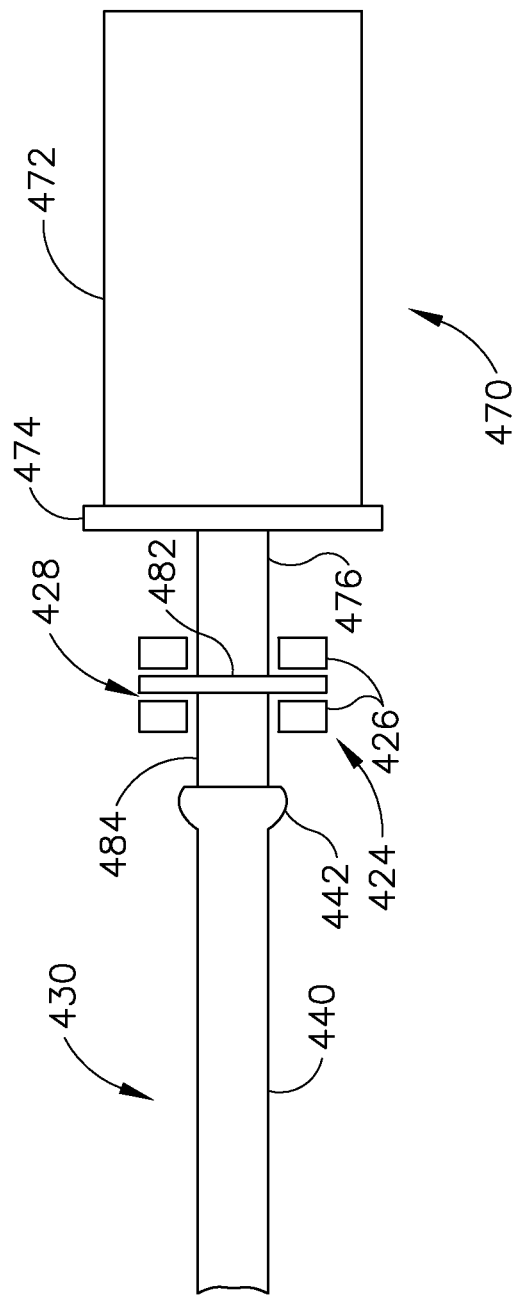
FIG. 10 depicts a top view of an exemplary transducer, forked portion of a trigger, and transmission assembly of the instrument shown in FIG. 9.

Trigger (420) is pivotably mounted to lower handle portion (410) with a trigger portion (422) extending out of lower handle portion (410) and a forked portion (424) within lower handle portion (410). Forked portion (424) comprises a pair of vertically oriented C-shaped members (426) (a side view of which is shown in FIG. 9 and a top view is shown in FIG. 10) configured to receive a disc (482) of transducer (470) in a disc recess (428) between the C-shaped members (426). C-shaped members (426) also permit outer tube (484) and/or horn (476) of transducer (470) to extend longitudinally through the gaps formed by the C-shape of C-shaped members (426).

Figure 11A:
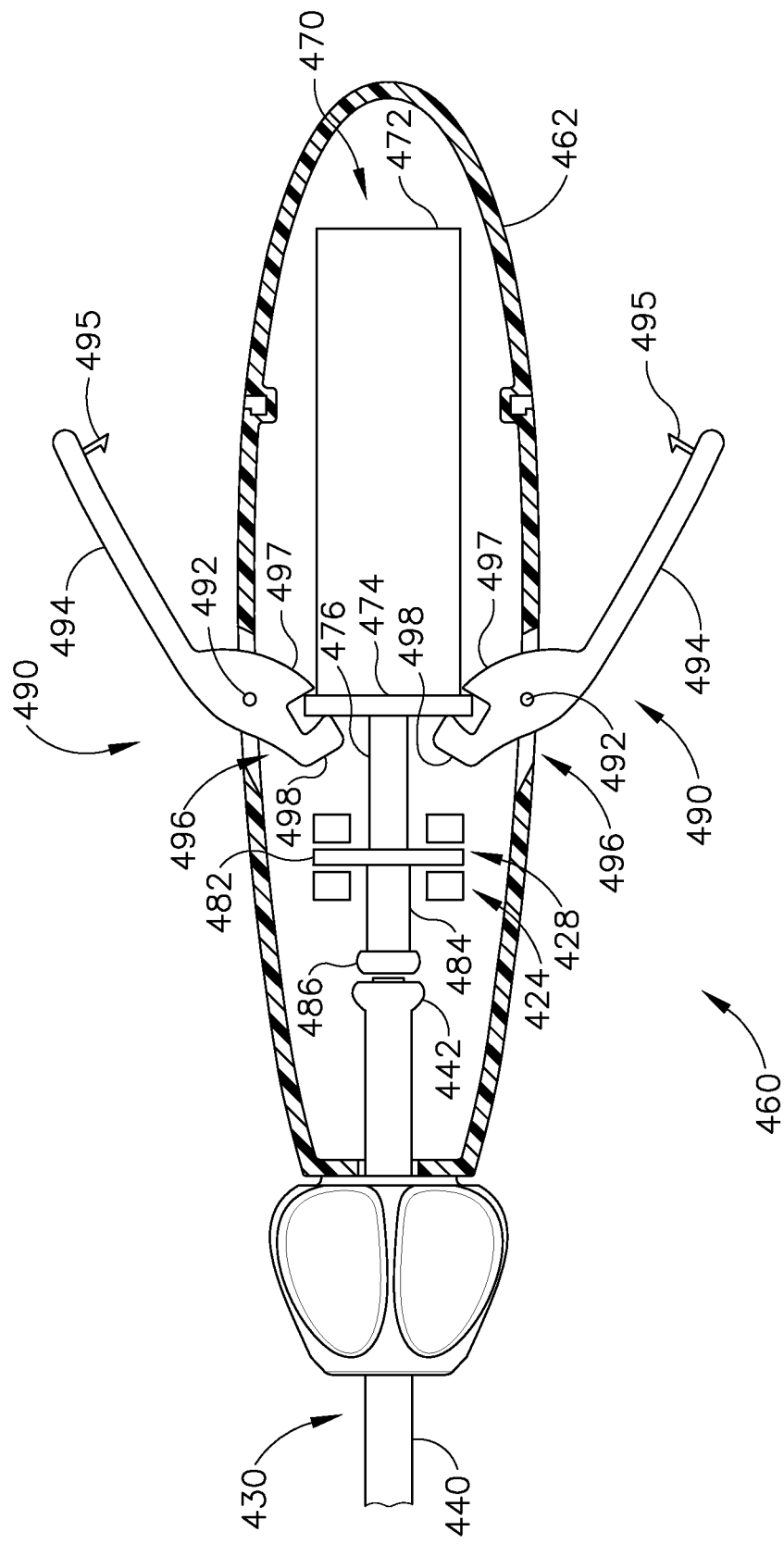
FIG. 11A depicts a top view of the instrument of FIG. 9 with a portion of the casing removed and showing the transducer unit inserted, but in an unlocked position.

Transducer unit (460) comprises a cover portion (462), a pair of bearing members (464), a pair of lever arms (490), shown in FIGS. 11A-11B, coupled to cover portion (462), and a transducer (470) rotatably mounted to cover portion (462) by bearing members (464). Cover portion (462) is configured to couple to lower handle portion (410), thereby forming a completed handle assembly (400). In some versions cover portion (462) couples to lower handle portion (410), such by snap fasteners, clips, clamps, screws, bolts, adhesives, or any other suitable coupling mechanism. In other versions, cover portion (462) may simply rest atop lower handle portion (410). Transducer (470) of the present example comprises a transducer body (472), a horn (476), a disc (482) coaxially disposed about horn (476), and an outer tube (484) coupled to the disc (482). As shown in FIG. 8, transducer (470) further comprises a cable (480) extending proximally from transducer body (472) and out of transducer unit (460) via an aperture in cover portion (462).

Transducer body (472) of the present example comprises an outer shell having a distal circumferential flange (474), as will be discussed in more detail later. Transducer body (472) encases a plurality of piezoelectric elements (not shown) compressed between a first resonator (not shown) and a second resonator (not shown) to form a stack of piezoelectric elements. The piezoelectric elements may be fabricated from any suitable material, for example, lead zirconate-titanate, lead meta-niobate, lead titanate, and/or any suitable piezoelectric crystal material, for example. Transducer body (472) further includes electrodes, including at least one positive electrode and at least one negative electrode, that are configured to create a voltage potential across the one or more piezoelectric elements, such that the piezoelectric elements convert the electrical power into ultrasonic vibrations.

Cable (480) is configured to electrically couple the electrodes to a power source, such as generator (20) discussed above. In some versions, cable (480) may be coupled to a power source contained within transducer unit (460) or to a power source within lower handle portion (410). In yet another version, a power source may be integrated into transducer (470). Horn (476) extends distally from transducer body (472) and includes a tapered recess (478) at a distal end. Tapered recess (478) is configured to couple to tapered shaft (452) of waveguide (450). When horn (476) is coupled to waveguide (450) via tapered recess (478) and tapered shaft (452), the ultrasonic vibrations produced by the stacks of piezoelectric elements are transmitted to waveguide (450). A blade (not shown) at the distal end of waveguide (450) oscillates according to the ultrasonic vibrations to simultaneously sever the tissue and denature the proteins in adjacent tissue cells, thereby providing a coagulative effect with relatively little thermal spread.

A disc (482) is coaxially disposed about horn (476) and is longitudinally actuatable relative to horn (476) and transducer body (472). In the present example, disc (482) is longitudinally retained on horn (476) by a raised portion (not shown) on horn (476) distal of disc (482). Accordingly, disc (482) is slidable on horn (476), but is still retained thereon. As another merely illustrative variation, disc (482) may include an internal annular recess configured to loosely receive a flange of horn (476), such that the recess permits disc (482) to slide relative to horn (476) while the flange restricts the longitudinal sliding range of disc (482) relative to horn (476). Disc (482) of the present example further includes an outer tube (484) fixedly coupled to disc (482) and extending distally from disc (482). Outer tube (484) includes a distal end having a flared portion (486). Flared portion (486) is configured to snap into flared snap-on connector (442) of outer shaft (440) when transducer (470) is coupled to waveguide (450). As noted above and shown best in FIG. 10, disc (482) is insertable into disc recess (428) of forked portion (424) of trigger (420). Disc (482), outer tube (484), and outer shaft (440) are actuated when trigger (420) is actuated by a user and when outer shaft (440) is coupled to outer tube (484). Accordingly, if the end effector includes a mechanically actuatable element, such as clamp arm (84) discussed above, then trigger (420) is operable to actuate that element via disc (482), outer tube (484), and outer shaft (440). Forked portion (424) of trigger (420) permits rotation of disc (482) and outer tube (484) while maintaining a longitudinally actuatable mechanical coupling. In some versions, disc (482) may include a force limiting mechanism, such as that disclosed in U.S. Pat. Pub. No. 2011/0015660, issued as U.S. Pat. No. 8,461,744 on Jun. 11, 2013. Of course other configurations and couplings for disc (482), trigger (420), and/or transducer (470) will be apparent to one of ordinary skill in the art in view of the teachings herein. For instance, in some versions disc (482), outer tube (484), and flared portion (486) may be a separate assembly from transducer (470). Alternatively, versions disc (482), outer tube (484), and flared portion (486) may be an assembly contained within casing (412).

FIGS. 11A-11B show the coupling sequence of transducer (470) to waveguide (450) and outer shaft (440) with a segment of cover portion (462) omitted for a better view. Lever arms (490) each comprise an elongated handle portion (494) and a camming member (496). Each camming member (496) includes a distally camming portion (497) and a proximally camming portion (498). Each camming member (496) is pivotably attached to casing portion (462) via pins (492) such that lever arms (490) may be rotated from an open position, in which handle portions (494) are angled outwardly from cover portion (462), shown in FIG. 11A, to a closed position, in which handle portions (494) are substantially parallel or flush against casing portion (462), shown in FIG. 11B. Recesses (not shown) in casing portion (462) may optionally be included for handle portions (494) to enter when in the closed position. Referring to FIG. 11A, when lever arms (490) are in the open position, distal camming portions (497) of camming members (496) are disengaged from flange (474). In this position, horn (476) and outer tube (484) are decoupled from waveguide (450) and outer shaft (440), respectively. When lever arms (490) are actuated to the closed position, distal camming portions (497) of camming members (496) engage flange (474) and actuate transducer (470) distally. As camming members (496) actuate flange (474) and transducer (470) distally, tapered shaft (452) engages tapered recess (478) and flared snap-on connector (442) snaps onto flared portion (486). In some instances, disc (482) is urged forward with horn (476) by a proximal raised portion (not shown). Alternatively, trigger (420) may be used actuate disc (482) to snap flared portion (486) into flared snap-on connector (442). Distal camming portions (497) may be sized such that a predetermined coupling force is applied to couple tapered recess (478) to tapered shaft (452) and flared portion (486) to snap-on connector (442) when lever arms (490) are in the closed position, as shown in FIG. 11B. For instance, distal camming portions (497) may be configured such that a coupling force of 5 to 10 pounds is provided, though this is merely exemplary. In some instances, the coupling force may be reduced to substantially zero (e.g., where tapered shaft (452) and tapered recess (478) engage at an antinode).

Handle portions (494) of the present example further include resilient insertable latches (495) to retain lever arms (490) against casing portion (462) when handle portions (494) are in the closed position. Latches (495) of the present example are selectively coupleable to recesses in casing portion (462). In some versions, other retention mechanisms may be used, such as snap fasteners, spring-loaded stops, screws, bolts, etc., to retain lever arms (490) in the closed position. When lever arms (490) are actuated back to the open position, proximal camming portions (498) engage transducer body (472) and/or flange (474) to urge transducer (470) proximally. This proximal urging of transducer (470) decouples tapered shaft (452) from tapered recess (478) and flared snap-on connector (442) unsnaps from flared portion (486).

When a user desires to couple transducer (470) to waveguide (450) and outer shaft (440), initially the user places transducer unit (460) atop lower handle portion (410) when lever arms (490) are in the open position, shown in FIG. 11A. Disc (482) of transducer (470) is also inserted into disc recess (428) of forked portion (424) of trigger (420), shown in FIGS. 9-10, thereby providing an initial mechanical coupling of disc (482) to trigger (420). As noted above, casing portion (462) of transducer unit (460) may also be coupled to lower handle portion (410). The user then actuates handle portions (494) of lever arms (490) to the closed position, thereby coupling tapered recess (478) to tapered shaft (452) and snapping flared portion (486) into flared snap-on connector (442). Handle portions (494) are locked in the closed position by latches (495). The mechanical coupling of outer shaft (440) to trigger (420) via disc (482) and forked portion (424) permits the user to actuate an actuatable portion of the end effector, if provided. In addition, the coupling of tapered recess (478) to tapered shaft (452) allows ultrasonic vibrations to be transmitted from transducer (470) to a blade of end effector when transducer (470) is activated. A user may use the assembled surgical instrument for a procedure.

To decouple handle assembly (400), the user actuates lever arms (490) back to the open position, thereby decoupling tapered recess (478) from tapered shaft (452) and unsnapping flared portion (486) from flared snap-on connector (442). The user may then remove transducer unit (460) for use with another lower handle portion (410). The used lower handle portion (410) may be disposed of, cleaned, and/or reclaimed. In some instances, transmission assembly (430) may be decoupled from lower handle portion (410). Such decoupling may allow a user to reuse lower handle portion (410) and only dispose of the dirty transmission assembly (430). Merely exemplary coupling and decoupling mechanisms for transmission assembly (430) are disclosed in U.S. patent application Ser. No. 13/269,870, entitled "Surgical Instrument with Modular Shaft and End Effector," filed Oct. 10, 2011, issued as U.S. Pat. No. 9,510,895 on Dec. 6, 2016, the disclosure of which is incorporated by reference herein. Thus, a user may quickly connect transducer (470) to waveguide (450) and also ensure an adequate connection between transducer (470) and waveguide (450) by using the camming lever arm coupling mechanism described herein.

Of course other configurations for a camming lever arm coupling mechanism will be apparent to one of ordinary skill in the art in view of the teachings herein. For instance, lever arms (490) may be replaced with longitudinal sliders that actuate transducer (470) distally and proximally via flange (474). In other versions, outer shaft (440), outer tube (484), disc (482), and trigger (420) may be omitted and only waveguide (450) and transducer (470) are used. In yet another version, transducer unit (460) may be permanently coupled to lower handle portion (410) and transducer (470) may be insertable through the top of casing portion (462). Still further configurations will be apparent to one of ordinary skill in the art in view of the teachings herein.

F. Exemplary Rotatable Clamshell Coupling Mechanism

Figure 12:
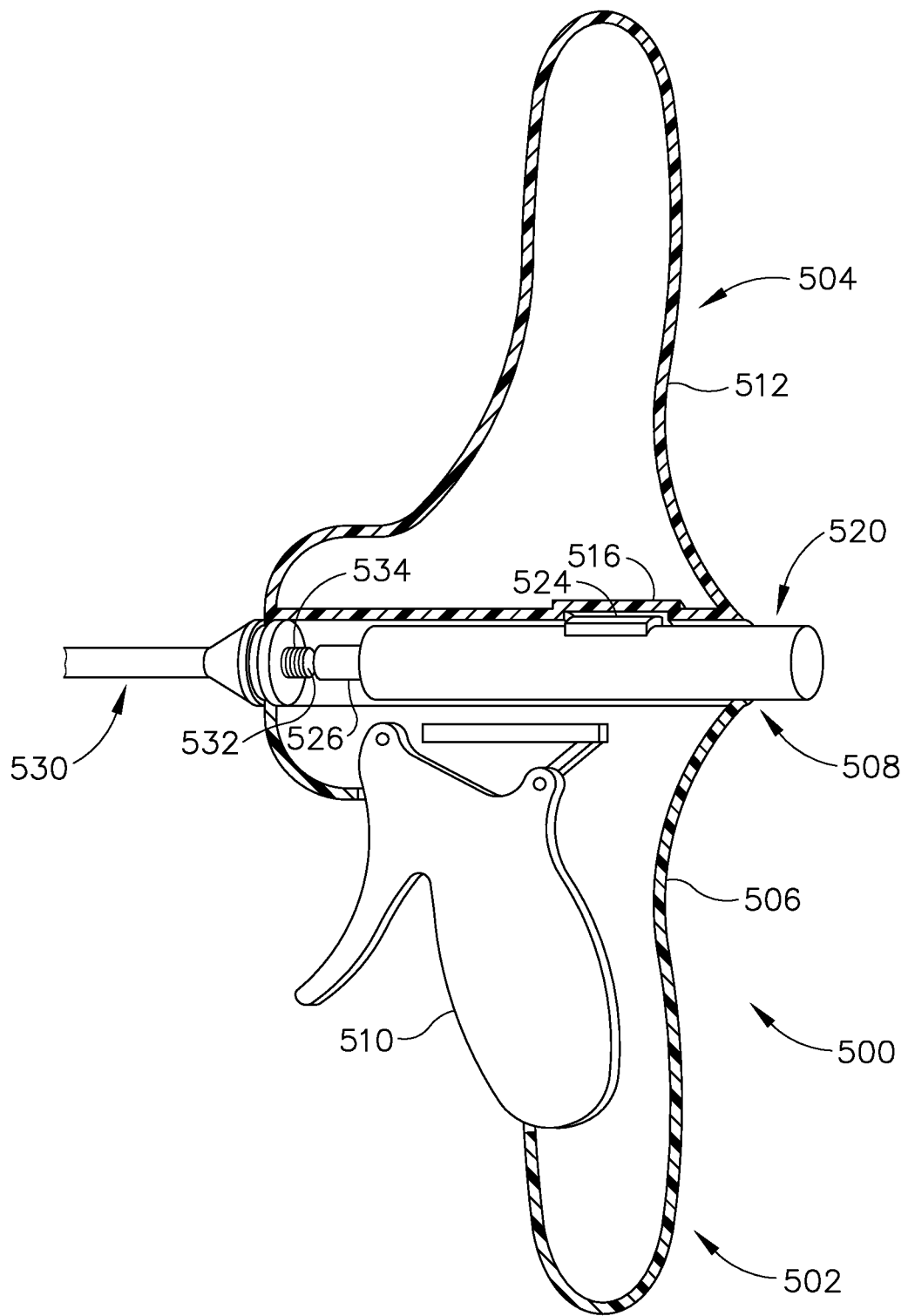
FIG. 12 depicts a left side view of an exemplary rotatable clamshell handle assembly shown in an open position.
Figure 13:
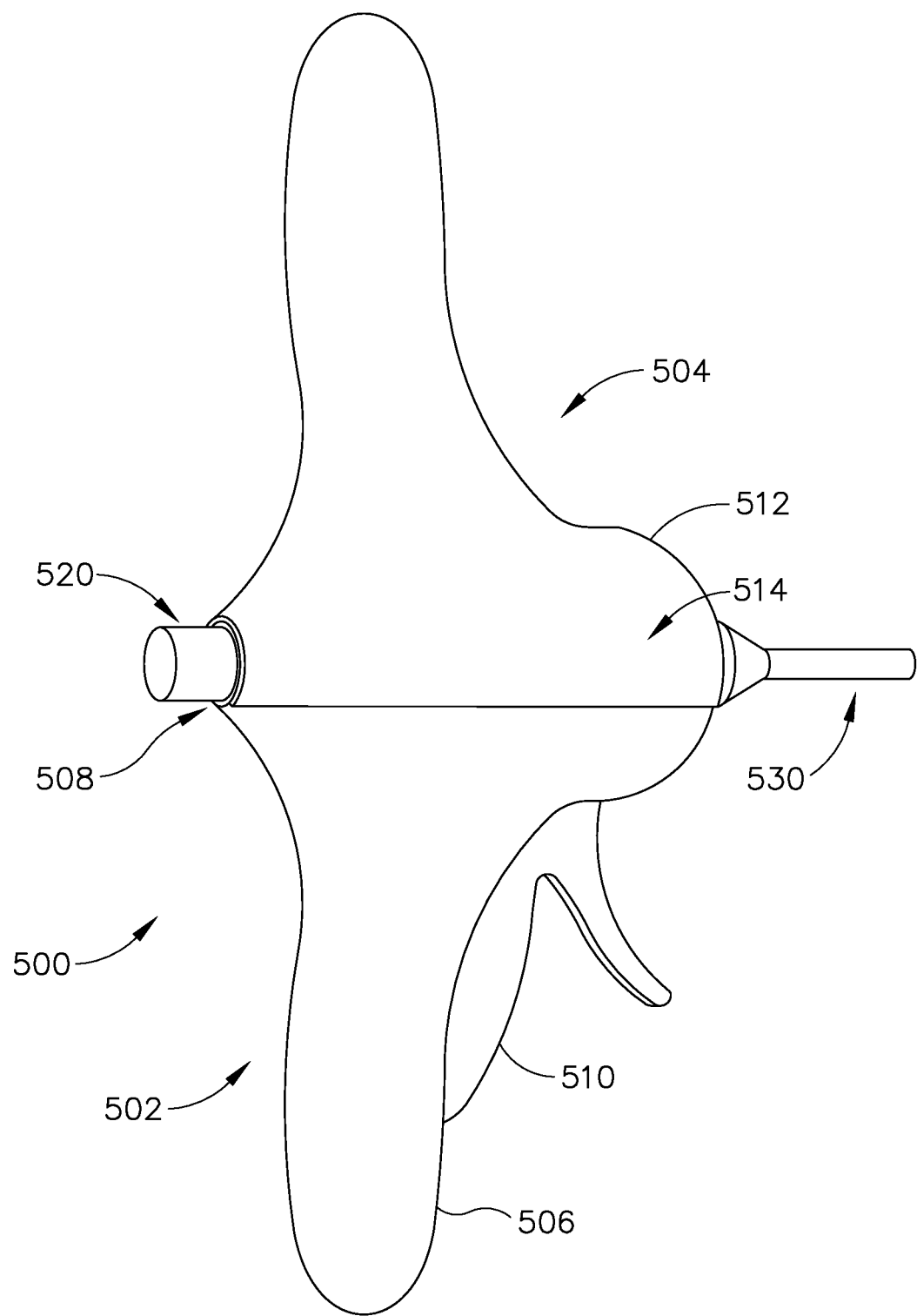
FIG. 13 depicts a right side view of the clamshell handle assembly of FIG. 12.

FIGS. 12-14 show another coupling mechanism for an exemplary handle assembly (500) to couple a transducer (520) to a transmission assembly (530). Transmission assembly (530) of the present example includes a waveguide (532) and an end effector (not shown) located on the distal end of transmission assembly (530). Transmission assembly (530) may be further configured in accordance with at least some of the teachings for transmission assembly (70) described above. The proximal end of waveguide (532) includes threading (534) configured to threadably couple to a horn (526) of transducer (520). Threading (534) of the present example is configured to torque horn (526) of transducer (520) onto waveguide (532) within 180 degrees of rotation, or a half turn. By way of example only, a quarter turn connector, a leur lock-type connector, and/or any other rotatable connection may be used to couple transducer (520) to waveguide (532). In the present example, transmission assembly (530) is fixed relative to handle assembly (500), though it should be understood that this is merely optional. For instance, transmission assembly (530) may be insertable into handle assembly (500) and selectively fixed to handle assembly (500) via a pin or latching mechanism (not shown). Merely exemplary detachable transmission assemblies are described in U.S. patent application Ser. No. 13/269,870, entitled "Surgical Instrument with Modular Shaft and End Effector," filed Oct. 10, 2011, issued as U.S. Pat. No. 9,510,895 on Dec. 6, 2016, the disclosure of which is incorporated by reference herein; and merely exemplary selective fixation mechanisms are described in U.S. patent application Ser. No. 13/269,899, entitled "Ultrasonic Surgical Instrument with Modular End Effector," filed Oct. 10, 2011, issued as U.S. Pat. No. 9,050,125 on Jun. 9, 2015, the disclosure of which is incorporated by reference herein. Transducer (520) comprises a transducer body (522) having a tab (524) and a horn (526) having a recess with threading that complements threading (534) of waveguide (532). Still other configurations for transmission assembly (530) and transducer (520) will be apparent to one of skill in the art in view of the teachings herein.

Handle assembly (500) of the present example comprises a first handle portion (502) and a second handle portion (504). Portions of handle assembly (500) have been omitted from FIG. 12 to provide a better view of transducer (520) and transmission assembly (530) within handle assembly (500). First handle portion (502) includes a first casing (506), a transducer recess (508) formed in first casing (506), and a trigger (510) operable to actuate a portion of transmission assembly (530), such as inner tubular actuator described above in reference to FIG. 1. First handle portion (502) may be further configured in accordance with at least some of the teachings of multi-piece handle assembly (60) described herein; U.S. Pat. Pub. No. 2006/0079874, now abandoned; U.S. Pat. Pub. No. 2007/0191713, now abandoned; U.S. Pat. Pub. No. 2007/0282333, now abandoned; U.S. Pat. Pub. No. 2008/0200940, now abandoned; U.S. Pat. Pub. No. 2011/0015660, issued as U.S. Pat. No. 8,461,744 on Jun. 11, 2013; U.S. Pat. No. 6,500,176; U.S. Pat. Pub. No. 2011/0087218, issued as U.S. Pat. No. 8,939,974 on Jan. 27, 2015; and/or U.S. Pat. Pub. No. 2009/0143797, issued as U.S. Pat. No. 8,419,757 on Apr. 16, 2013. In some versions trigger (510) may be omitted. As shown best in FIG. 14, transducer recess (508) is a semi-cylindrical recess defined by a semi-cylindrical portion of first casing (506) that is configured to receive a portion of transducer (520) therein. An opening in transducer recess (508) permits tab (524) of transducer (520) to enter a notch (516) formed in second casing (512), as will be described in greater detail below.

Second handle portion (504) of the present example includes a second casing (512) having a rotatable hinge member (514), shown in FIGS. 13-14. In the present example, rotatable hinge member (514) is integrally formed with second casing (512). Rotatable hinge member (514) wraps around the semi-cylindrical portion of first casing (506) defining transducer recess (508), thereby forming a slightly larger semi-cylindrical portion, as shown in FIG. 14. Second casing (512) further comprises a notch (516) configured to receive tab (524) of transducer (520), as shown in FIG. 12 and FIG. 14 (shown in phantom). Second casing (512) and first casing (506) further include interference fittings (not shown) to couple first casing (506) to second casing (512) when second casing (512) is rotated into a locked position, as will be described below. Of course other attachment mechanisms, such as snap fasteners, pins, clips, clamps, screws, bolts, adhesives, etc., may be used to couple second casing (512) to first casing (506).

When a user desires to coupled transducer (520) to transmission assembly (530), initially the user places transducer (520) within transducer recess (508) and aligns tab (524) with notch (516). The user also initially engages threading (534) of waveguide (532) with the threads of horn (526) of transducer (520). Such an initial, unlocked position is shown in FIGS. 12-14. The user then rotates second casing (512) about the semi-cylindrical portion of first casing (506) defining transducer recess (508) via rotatable hinge member (514). As second casing (512) is rotated, notch (516) engages tab (524) and rotates transducer (520). Accordingly, horn (526) rotates and torques down onto threading (534) of waveguide (532), thereby coupling transducer (520) to waveguide (532). Second casing (512) is then coupled to first casing (506) via the interference fittings, resulting in the locked position for handle assembly (500). The user may then use the assembled surgical instrument. In some versions, a torque limiting device may be included on first casing (506) and/or second casing (512) to ensure transducer (520) is not overtightened to waveguide (532).

To decouple transducer (520) from transmission assembly (530), initially second casing (512) is decoupled from first casing (506). The user rotates second casing (512) about the semi-cylindrical portion of first casing (506) defining transducer recess (508) via rotatable hinge member (514) back to the unlocked position shown in FIGS. 12-14. When first casing (506) and second casing (512) are back in the unlocked position, the user may then remove transducer (520) from within handle assembly (500) for reuse, cleaning, and/or reclamation. Handle assembly (500) and transmission assembly (530) may be disposed of, cleaned, and/or reclaimed. As noted above, in some versions transmission assembly (530) is detachable from handle assembly (500). In such instances, handle assembly (500) may also be reusable while transmission assembly (530) is disposed of. Thus, a user may quickly connect transducer (520) to transmission assembly (530) and also ensure an adequate connection between transducer (520) and waveguide (532) by using the rotatable clamshell coupling mechanism described herein.

Of course, as with the other coupling mechanisms described herein, other configurations for the rotatable clamshell coupling mechanism will be apparent to one of ordinary skill in the art in view of the teachings herein. For instance, in some versions, nested frustoconical features may be used to couple transducer (520) to waveguide (532) instead of threading (534) described above. Merely exemplary frustoconical features include cone (162) and conical recess (152) shown and described in reference to FIG. 2 above. For a rotatable clamshell incorporating the frustoconical coupling features, second casing (512) may include a cam feature associated with tab (524) that drives transducer (520) distally relative to first casing (506) when second casing (512) is rotated towards first casing (506). Accordingly, when second casing (512) is fully rotated toward first casing (506), the cam feature urges and secures transducer (520) to waveguide (532).

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a casing;
   (b) a waveguide longitudinally extending along a central longitudinal axis and having a proximal end, wherein the proximal end comprises a longitudinal recess extending along the central longitudinal axis and a first transaxial hole transecting the longitudinal recess through the central longitudinal axis;
   (c) a transducer comprising a horn insertable into the longitudinal recess and a second transaxial hole;
   (d) a first pin and lever assembly comprising:
      i. a first lever rotatably coupled to the casing, and
      ii. a first pin portion having a first longitudinal width and actuatable by the first lever; and
   (e) a second pin and lever assembly comprising:
      i. a second lever rotatably coupled to the casing, and
      ii. a second pin portion having a second longitudinal width and actuatable by the second lever,
      wherein the first and second pin portions are configured to selectively move from a first position to a second position,
   wherein the first and second pin portions in the first position extend through the first and second transaxial holes such that at least one of the first and second pin portions transversely extends through the central longitudinal axis and the first and second portions engage together to collectively define a third longitudinal width larger than respectively each of the first and second longitudinal widths to thereby couple the transducer to the waveguide, and
   wherein the first and second pin portions in the second position are positioned transversely away from the longitudinal axis to thereby decouple the transducer from the waveguide.

2. The surgical instrument of claim 1 wherein the first pin portion comprises a first pin end having a first ramped portion, and wherein the second pin portion comprising a second pin end having a second ramped portion.

3. The surgical instrument of claim 2 wherein the first ramped portion is defined by a first angle, wherein the second ramped portion is defined by a second angle, and wherein the first angle and the second angle are alternate interior angles such that second ramped portion and first ramped portion are parallel planar portions.

4. The surgical instrument of claim 3, wherein the first ramped portion and the second ramped portion are configured to abut against each other within the second transaxial hole when the first pin portion and the second pin portion are in a first position.

5. The surgical instrument of claim 4, wherein the first pin portion and the second pin portion are configured to actuate from the first position to a second position.

6. The surgical instrument of claim 5, wherein the first pin portion and the second pin portion are configured to urge the waveguide toward the transducer when the first pin portion and the second pin portion are in the first position.

7. The surgical instrument of claim 6, wherein the surgical instrument further comprises a first torsion spring and a second torsion spring.

8. The surgical instrument of claim 7, wherein the first torsion spring is connected to the casing and the first lever, wherein the second torsion spring is connected to the casing and the second lever.

9. The surgical instrument of claim 8, wherein the first torsion spring is configured to bias the first pin portion toward the first position, wherein the second torsion spring is configured to bias the second pin portion toward the first position.

10. The surgical instrument of claim 9, wherein the first pin and lever assembly further comprises a first handle unitarily coupled to the first lever, wherein the second pin and lever assembly further comprises a second handle unitarily coupled to the second lever, wherein the first handle is configured to rotate the first lever about the casing such that the first pin portion is in the second position, wherein the second handle is configured to rotate the second lever about the casing such that the second pin portion is in the second position.

11. The surgical instrument of claim 6, wherein the first lever is configured to disengage the first pin portion when the first pin portion is in the first position, wherein the second lever is configured to disengage the second pin portion when the second pin portion is in the first position.

12. The surgical instrument of claim 1, wherein the casing further comprises a first aperture and a second aperture, wherein the first aperture is configured to receive the first pin portion, wherein the second aperture is configured to receive the second pin portion.

13. The surgical instrument of claim 1, wherein the first lever portion comprises an L-shaped member defining a ledge, wherein the first pin portion comprises a wheel located within the L-shaped member, wherein the wheel is configured to translate relative to the ledge.

14. The surgical instrument of claim 1, wherein the first and second pin portions in the first position abut against each other such that at least one of the first and second pin portions is longitudinally urged along the central longitudinal axis toward the waveguide to thereby urge the waveguide toward the transducer.

15. The surgical instrument of claim 14, wherein the first and second pin portions in the first position abut against each other such that the first and second pin portions are longitudinally urged in opposite longitudinal directions along the central longitudinal axis to thereby urge the waveguide toward the transducer.

16. The surgical instrument of claim 15, wherein the first and second pin portions in the first position abut against each other at the central longitudinal axis.

17. A surgical instrument comprising:
(a) a body;
(b) a waveguide longitudinally extending along a central longitudinal axis in a longitudinal direction and having a proximal end, wherein the proximal end comprises a longitudinal recess and a first transaxial hole;
(c) a transducer comprising a horn and a second transaxial hole, wherein the horn is insertable into the longitudinal recess;
(d) a first pin assembly comprising:
  i. a first actuator movably coupled to the casing, and
  ii. a first pin portion actuatable by the first actuator; and
(e) a second pin assembly comprising:
  i. a second actuator movably coupled to the casing, and
  ii. a second pin portion actuatable by the second actuator,
wherein the first pin portion and the second pin portion are configured to actuate from a first position to a second position, wherein the first pin portion and the second pin portion are located within both the first transaxial hole and the second transaxial hole in the first position, wherein the first pin portion and the second pin portion are located outside both the first transaxial hole and the second transaxial hole in the second position, wherein the transducer is configured to transmit ultrasonic vibrations to the waveguide when the first pin portion and the second pin portion are in the first position,
wherein the first and second pin portions in the first position abut against each other such that at least one of the first and second pin portions is longitudinally urged in the longitudinal direction toward the waveguide to thereby urge the waveguide toward the transducer.

18. The surgical instrument of claim 17, wherein the first actuator comprises a first lever pivotably coupled to the casing, wherein the second actuator comprises a lever pivotably coupled to the casing.

19. The surgical instrument of claim 17, wherein the first pin portion has a first longitudinal width, wherein the second pin portion has a second longitudinal width, and wherein the first and second pin portions in the first position abut against each other to collectively defines a third longitudinal width larger than respectively each of the first and second longitudinal widths.

20. A surgical instrument comprising:
(a) a casing comprising:
  i. a first aperture, and
  ii. a second aperture;
(b) a waveguide longitudinally extending along a central longitudinal axis in a longitudinal direction and having a proximal end, wherein the proximal end comprises a longitudinal recess and a first transaxial hole;
(c) a transducer comprising a horn and a second transaxial hole, wherein the horn is insertable into the longitudinal recess;
(d) a first pin assembly comprising:
  i. a first actuator movably coupled to the casing, and
  ii. a first pin portion actuatable by the first actuator, wherein the first pin portion is disposed within the first aperture; and
(e) a second pin assembly comprising:
  i. a second actuator movably coupled to the casing, and
  ii. a second pin portion actuatable by the second actuator, wherein the second pin portion is disposed with the second aperture,
wherein the first and second pin portions are configured to selectively move from a first position to a second position,
wherein the first and second pin portions in the first position engage together and overlap in the longitudinal direction to thereby couple the transducer to the waveguide, and
wherein the first and second pin portions in the second position do not engage and do not overlap in the longitudinal direction to thereby decouple the transducer from the waveguide.

* * * * *